US008691851B2

(12) United States Patent
Pervaiz et al.

(10) Patent No.: US 8,691,851 B2
(45) Date of Patent: Apr. 8, 2014

(54) LANTHANIDE METAL COMPLEXES USEFUL IN TREATING CANCER

(75) Inventors: Shazib Pervaiz, Singapore (SG); Sanjiv Kumar Yadav, Singapore (SG); Alan Prem Kumar, Singapore (SG); Chun Chi Carolyn Ng, Singapore (SG)

(73) Assignee: National University of Singapore, Singapore (SG)

( * ) Notice: Subject to any disclaimer, the term of this patent is extended or adjusted under 35 U.S.C. 154(b) by 24 days.

(21) Appl. No.: 13/262,561

(22) PCT Filed: Apr. 1, 2010

(86) PCT No.: PCT/SG2010/000132
§ 371 (c)(1),
(2), (4) Date: Dec. 9, 2011

(87) PCT Pub. No.: WO2010/114493
PCT Pub. Date: Oct. 7, 2010

(65) Prior Publication Data
US 2012/0077792 A1    Mar. 29, 2012

Related U.S. Application Data

(60) Provisional application No. 61/165,636, filed on Apr. 1, 2009.

(51) Int. Cl.
*A01N 43/40* (2006.01)
*A61K 31/44* (2006.01)
*A01N 59/20* (2006.01)
*A61K 33/34* (2006.01)

(52) U.S. Cl.
USPC .......................................... 514/345; 424/638

(58) Field of Classification Search
None
See application file for complete search history.

(56) References Cited

U.S. PATENT DOCUMENTS

| 3,971,725 | A | 7/1976 | Douglass |
| 4,041,033 | A | 8/1977 | Douglass |
| 4,122,085 | A | 10/1978 | Douglass |

OTHER PUBLICATIONS

Wang et al. J. Coord. Chem. 1993 (28) 167-172.*
Wang et al. Journal of Coordination Chemistry 1993 (28) 167-172.*
Brown, G., et al., "Purine N-Oxides. XV. The Synthesis of 6-Mercaptopurine 3-N-Oxide. Its Chemotherapeutic Possibilities", "J. Med. Chem.", Mar. 1965, pp. 190-195, vol. 8, No. 2.
Cande, C., et al., "Apoptosis-inducing factor (AIF): key to the conserved caspase-independent pathways of cell death?", "Journal of Cell Science", 2002, pp. 4727-4734, vol. 115, No. 24.
Ding, G., et al., "Cardiac peroxisome proliferator-activated receptor γ is essential in protecting cardiomyocytes from oxidative damage", "Cardiovascular Research", 2007, pp. 269-279, vol. 76, No. 2.
Kabeya, Y., et al., "LC3, a mammalian homologue of yeast Apg8p, is localized in autophagosome membranes after processing", "The European Molecular Biology Organization Journal", 2000, pp. 5720-5728, vol. 19, No. 21.
Kim, J., et al., "Evaluation of Polycyclic Aromatic Hydrocarbons in the Activation of Early Growth Response-1 and Peroxisome Proliferator Activated Receptors", "Toxicological Sciences", 2005, pp. 585-593, vol. 85.
Lorenzo, H., et al., "Apoptosis inducing factor (AIF): a phylogenetically old, caspase-independent effector of cell death", "Cell Death and Differentiation", 1999, pp. 516-524, vol. 6.
Marlow, L., et al., "Reactivation of Suppressed RhoB is a Critical Step for the Inhibition of Anaplastic Thyroid Cancer Growth", "Cancer Research", 2009, pp. 1536-1544, vol. 69, No. 4.
Mosmann, T., "Rapid Colorimetric Assay for Cellular Growth and Survival: Application to Proliferation and Cytotoxicity Assays", "Journal of Immunological Methods", 1983, pp. 55-63, vol. 65.
Niu, D., et al., "Synthesis and crystal structure of Pr(mpo)3(DMSO)2 (Hmpo = 2-mercaptopyridine N-oxide)", "Journal of Chemical Crystallography", Mar. 2004, pp. 195-198, vol. 34, No. 3.
Sugiura, K., et al., "Purine N-Oxides XIX. On the Oncogenic N-Oxide Derivatives of Guanine and Xanthine and a Nononcogenic Isomer of Xanthine N-Oxide", "Cancer Research", May 1967, pp. 925-931, vol. 27, No. 1.
Tedeschi, C., et al., "First crystal structure of a Tb3+ complex derived from an aromatic hydroxamate ligand: sensitized luminescence properties", "New J. Chem.", 2000, pp. 735-737, vol. 24.
Tedeschi, C., et al., "A solid-state study of eight-coordinate lanthanide(III) complexes (Ln = Eu, Gd, Tb, Dy) with 1-hydroxy-2-pyridinone", "Dalton Transactions", 2003, pp. 1738-1745, vol. 9.
Teresi, R., et al., "Increased PTEN expression due to transcriptional activation of PPARγ by Lovastatin and Rosiglitazone", "Int. J. Cancer", 2006, pp. 2390-2398, vol. 118, No. 10.

* cited by examiner

*Primary Examiner* — Jeffrey S. Lundgren
*Assistant Examiner* — Michael Schmitt
(74) *Attorney, Agent, or Firm* — Hultquist, PLLC; Steven J. Hulquist

(57) ABSTRACT

The present invention relates to a compound of formula (I). Provided is also a method of killing a cell that comprises administering the compound of formula (I). Provided is also a method of treating cancer or diabetes in a mammal that comprises administering the compound of formula I and respective pharmaceutical compositions thereof.

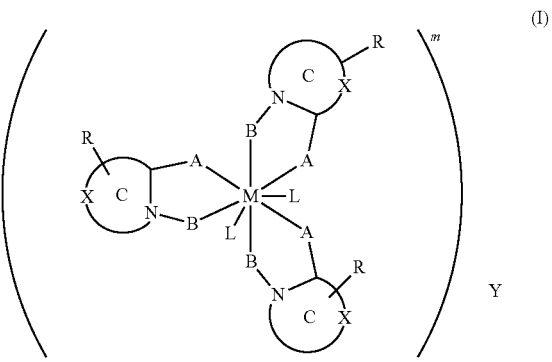

1 Claim, 20 Drawing Sheets

SHEP1

SHEP1

SHEP1

| Time (h) | 24 | | |
|---|---|---|---|
| Pr-MPO uM | 0 | 5 | 10 |

SHEP1

SHEP1

SHSY5Y

| Time (h) | 24 | | | | | |
|---|---|---|---|---|---|---|
| Fractions | Mitochondra | | | Cytosol | | |
| Pr-MPO uM | 0 | 5 | 10 | 0 | 5 | 10 |

VDAC

Bax

Cytochrome C $\beta$-actin

CuZnSOD

| Time (h) | 18 | | | | | | 24 | | | | | |
|---|---|---|---|---|---|---|---|---|---|---|---|---|
| Fractions | Cytosol | | | Nucleus | | | Cytosol | | | Nucleus | | |
| Pr-MPO uM | 0 | 5 | 10 | 0 | 5 | 10 | 0 | 5 | 10 | 0 | 5 | 10 |

PARP

AIF

CuZnSOD $\beta$-actin

SHEP1

| Time (h) | 4 | | | 8 | | | 18 | | |
|---|---|---|---|---|---|---|---|---|---|
| Pr-MPO uM | 0 | 5 | 10 | 0 | 5 | 10 | 0 | 5 | 10 |

LC3 I
LC3 II $\beta$-actin

SHSY5Y

| Time (h) | 4 | | | Blank | 8 | | | 18 | | |
|---|---|---|---|---|---|---|---|---|---|---|
| Pr-MPO uM | 0 | 5 | 10 | | 0 | 5 | 10 | 0 | 5 | 10 |

LC3 I
LC3 II $\beta$-actin

LANTHANIDE METAL COMPLEXES USEFUL IN TREATING CANCER

CROSS-REFERENCE TO RELATED APPLICATIONS

This is a U.S. national phase under the provisions of 35 U.S.C. §371 of International Patent Application No. PCT/SG10/00132 filed Apr. 1, 2010, which in turn claims the benefit of priority of U.S. Provisional Patent Application No. 61/165,636 filed Apr. 1, 2009. The disclosures of such international patent application and U.S. priority provisional patent application are hereby incorporated herein by reference in their respective entireties, for all purposes.

FIELD OF THE INVENTION

The present invention relates to a compound that can act as a ligand for the proliferation activator receptor-gamma (PPARγ) and methods of its use. The invention also provides a method of killing a cell using the compound as well as a pharmaceutical composition of the compound.

BACKGROUND OF THE INVENTION

Cancer is a major cause of death worldwide, being the second-leading cause of death in developed countries, and even the number one cause of death in e.g. Australia, Japan, Korea, Singapore and the male population of the United Kingdom and Spain. The number of individuals who develop cancer each year is increasing. This increase in prevalence in cancer is comparable with the increased number of individuals suffering from diabetes. Diabetes is a chronic and serious global health problem and affects millions of people worldwide. Diabetes often results in substantial morbidity and mortality, mainly from cardiovascular complications, eye and kidney diseases and limb amputations. The increase in prevalence of such diseases is attributed to population growth, aging and urbanization. Therefore, there is a need to develop therapeutic agents that target intracellular proteins which can lower the incidence of cancer and diabetes.

One such class of intracellular proteins is the nuclear receptor proteins which include the peroxisome proliferator activated receptors (PPARs). PPARs are ligand activated transcription factors belonging to the nuclear receptor superfamily that includes receptors for steroids, thyroid hormone, vitamin D, and retinoic acid. The functional role of PPARs ranges from modulation of glucose and lipid homeostasis to regulation of cell growth and differentiation. For example, it was established that PPAR-gamma (PPARγ) is a dominant regulator of adipocyte differentiation. The PPARγ can also inhibit the proliferation of malignant cells from different lineages such as breast, prostate, colorectal, non-small cell lung, pancreatic, bladder and gastric carcinoma. For this reason, numerous endogenous ligands for the PPARγ have been synthesized for developing therapeutic agents to target a variety of diseases including diabetes and cancer. For example, drugs such as rosiglitazone (RGZ), troglitazone (TGZ), ciglitazone (CGZ) and pioglitazone (PGZ) are a class of thiazolidinedione (TZD) drugs that selectively bind and activate PPARγ to treat diabetes and other related diseases. However, the main side effect of all thiazolidinediones is significant water retention, leading to edema in some and potentially heart failure in others.

Although further studies have been carried out to identify agents useful for treating diseases and pathological conditions affected by nuclear receptors and the associated co-factors, most of these synthetic ligands exhibit harmful side effects, which have limited their use in the clinic. Therefore, identification of new ligands that have a therapeutic purpose for treating the above diseases is highly desirable.

Accordingly, it is an object of the invention to provide a compound that acts a ligand of the PPARγ receptor.

It is a further object of the invention to provide a compound that can be a potent activator of the PPARγ receptor.

Another object of the invention is to provide a pharmaceutical composition that can ameliorate the disadvantages mentioned above.

SUMMARY OF THE INVENTION

In a first aspect, the invention provides a compound of the formula (I):

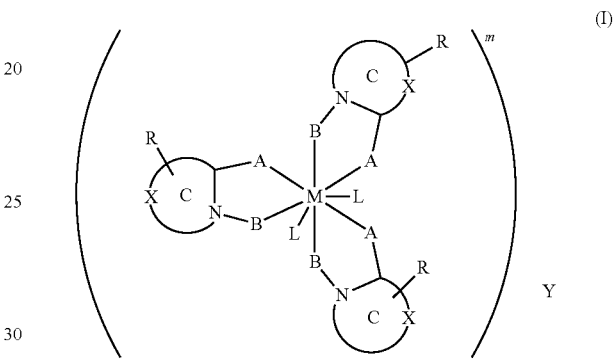

wherein
M is a lanthanide element;
C is a ring system of the formula:

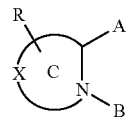

the ring system comprising 5 to 8 main chain atoms, wherein the ring system can be fused to at least one 5- to 8-membered ring, wherein one or more of the atoms in the ring system can be substituted by a group X, wherein X is selected from the group consisting of S, O, N, NH, NHR$^4$, SO or SO$_2$, and wherein one or more of the atoms in the ring system can carry a substituent R;
R is independently selected from the group consisting of hydrogen, hydroxyl, alkyl, alkylene, alkenyl, alkynyl, acyl, cycloalkyl, cycloalkenyl, substituted or unsubstituted aryl, substituted or unsubstituted heteroaryl, substituted or unsubstituted heteroalicyclyl, halogen, carbonyl, thiocarbonyl, O-carbamyl, O-thiocarbomyl, O-carboxy, isocyanato, thiocyanato, silyl, amino, mono- and di-substituted amino groups, perhaloalkyl, sulfonyl, sulfonamide, thio, —CF$_3$, —CO, —CN, —COON, —CONH$_2$, —SH, —Se, —SO$_2$, —N═N, —N═O, and OCF$_3$;
A and B are electron donating units coordinated to M;
L is a complexing moiety;
m is +1, +2, +3 or +4; and
Y is an anion, or a combination of anions that balances m;
with the proviso that the following compounds are excluded: samarium (2-mercaptopyridine N-oxide)(dimethyl sulfoxide) and praseodymium (2-mercaptopyridine N-oxide)(dimethyl sulfoxide).

In a second aspect, the invention provides a method of preparing a compound of formula (I), the method comprising forming a solution of a compound of the formula $M_aO_b$ under acidic conditions, wherein M is a lanthanide element, a=1 to 6 and b=3 to 11; increasing the pH of the solution by adding alkali; and adding a compound of the formula

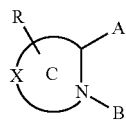

to the reaction mixture in the presence of a complexing moiety L, thereby obtaining the compound of formula (I).

In a third aspect, the invention provides a method of killing a cell. The method includes administering to the cell a compound of the formula (I), wherein the compounds include samarium (2-mercaptopyridine N-oxide)(dimethyl sulfoxide) and praseodymium (2-mercaptopyridine N-oxide)(dimethyl sulfoxide).

In a fourth aspect, the invention provides a method of treating a mammal having cancer. The method includes administering to the mammal a compound of the formula (I), wherein the compound includes samarium (2-mercaptopyridine N-oxide)(dimethyl sulfoxide) and praseodymium (2-mercaptopyridine N-oxide)(dimethyl sulfoxide).

In a fifth aspect, the invention provides a method of treating a mammal having diabetes. The method includes administering to the mammal a compound of the formula (I), wherein the compound includes samarium (2-mercaptopyridine N-oxide)(dimethyl sulfoxide) and praseodymium (2-mercaptopyridine N-oxide)(dimethyl sulfoxide).

In a sixth aspect, the invention provides a pharmaceutical composition. The pharmaceutical composition includes a compound of formula (I) wherein the compound includes samarium (2-mercaptopyridine N-oxide)(dimethyl sulfoxide) and praseodymium (2-mercaptopyridine N-oxide)(dimethyl sulfoxide). The pharmaceutical composition further includes a carrier or diluent.

In a seventh aspect, the invention provides a method of treating a mammal having cancer or diabetes. The method includes administering to the mammal the pharmaceutical composition as described above.

In an eighth aspect, the invention provides a method of modulating the expression of a PPAR-γ target protein in a cell. The method includes contacting the cell with a compound of formula (I), wherein the compounds samarium (2-mercaptopyridine N-oxide)(dimethyl sulfoxide) and praseodymium (2-mercaptopyridine N-oxide)(dimethyl sulfoxide) that are excluded in the first aspect are included.

In a ninth aspect, the invention provides a method of identifying a candidate compound capable of preventing, inhibiting, arresting or reversing tumourigenesis in a cell and/or inducing apoptosis in a tumor cell. The method includes introducing the compound into a cell capable of expressing a PPAR-γ target protein. The method further includes determining the expression of the PPAR-γ target protein. An altered/modulated expression of the PPAR-γ target protein is an indication that the compound is capable of preventing, inhibiting, arresting or reversing tumourigenesis in a cell and/or inducing apoptosis in a tumor cell.

In a tenth aspect, the invention provides a method of identifying a candidate compound capable of activating a PPAR-γ receptor protein in a cell. The method includes introducing the compound into a cell expressing PTEN, MnSOD and RhoB. The method further includes determining the expression of PTEN, MnSOD and RhoB. An increased expression of PTEN and RhoB and a decreased expression of RhoB indicate that the compound is capable of activating the PPAR-γ receptor protein.

These and other aspects of the present invention will now be described with reference to the detailed description when considered in conjunction with the non-limiting examples and the accompanying drawings.

BRIEF DESCRIPTION OF THE DRAWINGS

As shown in FIG. 20B, Pr-MPO induces activation in response specifically to transfection of pCMX-Gal-mPPARγ-LBD, but not to other isoforms of PPARs.

As shown in FIG. 23, AIF was translocated into the nucleus 24 hr after treatment with Pr-MPO.

DETAILED DESCRIPTION OF THE INVENTION

Figure 1:
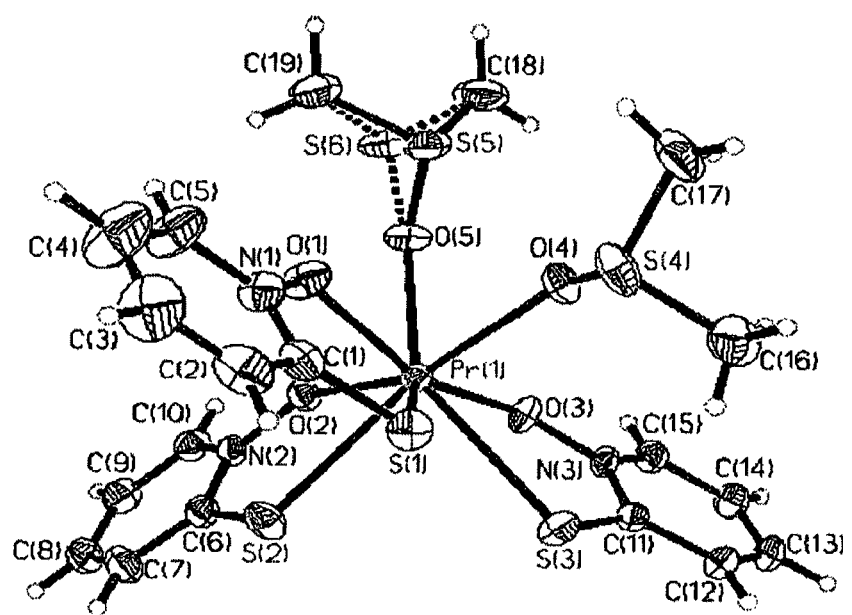
FIG. 1 shows a schematic representation of the molecular structure of $C_{19}H_{24}N_3O_5S_5Pr$.

The present invention is based on the finding that a compound of the formula (I), including the compounds samarium (2-mercaptopyridine N-oxide)(dimethyl sulfoxide) and praseodymium (2-mercaptopyridine N-oxide)(dimethyl sulfoxide), can bind to PPARγ, for example the ligand binding domain of PPARγ with high specificity. Therefore, the inventors also found that the compound of the formula (I) can be a potent activator of PPARγ. In addition, the activated PPARγ can induce cell killing in particularly in cancer cells for example. Therefore, there is a likely correlation between cell death and PPARγ activation. The inventors have also found that the cell death is likely to be caspase-independent.

There are generally three types of PPAR which are identified as PPARα (accession number: NM_005036), PPARβ/δ (accession number: XM_004285) and PPARγ (accession number: XM_003059). These PPAR subtypes share a highly conserved DNA binding domain and bind to specific DNA sequences of target genes. These specific DNA sequences are known as peroxisome proliferator response elements (PPREs). Once a ligand binds with the PPAR, the PPAR translocates from the cytoplasm to the nucleus of the cell, and forms a heterodimer with a retinoid X receptor (RXR). The PPAR/RXR complex promotes recruitment of transcriptional co-activators and binds to the PPREs to modulate the transcription of the target genes regulating different physiological processes. Therefore, the PPAR is activated in the cell upon binding to a ligand.

The compounds as described in the present invention, including the compounds samarium (2-mercaptopyridine N-oxide)(dimethyl sulfoxide) and praseodymium (2-mercaptopyridine N-oxide)(dimethyl sulfoxide), can act as a ligand to the PPARγ. Accordingly, the present invention provides a compound of the formula (I)

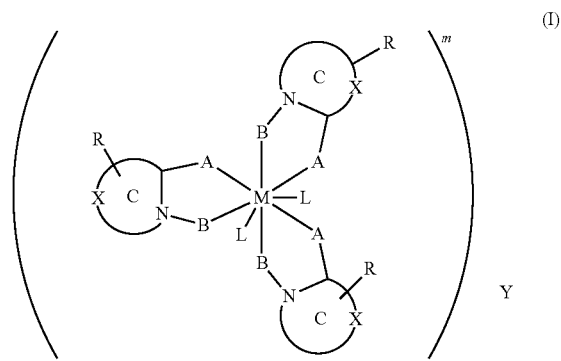

with the proviso that the compounds samarium (2-mercaptopyridine N-oxide)(dimethyl sulfoxide) and praseodymium (2-mercaptopyridine N-oxide)(dimethyl sulfoxide) are excluded. Praseodymium (2-mercaptopyridine N-oxide) (dimethyl sulfoxide), also referred to in the following as Pr(mpo)$_3$(DMSO)$_2$ has the empirical formula C$_{19}$H$_{24}$N$_3$O$_5$S$_5$Pr and has been described in Niu, De-Zhong et al., *Journal of Chemical Crystallography* (2004) 34(3), 195-198. In this context, the inventors have found that the compounds as described herein, including Pr(mpo)$_3$(DMSO)$_2$ can bind and activate the PPARγ in a cell. In addition, the compounds as described herein, including Pr(mpo)$_3$(DMSO)$_2$, can, for example, induce cell killing, in particularly in cancer cells. In the compound of the formula (I), the ring system C is of the formula:

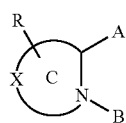

The term "ring" as described herein refers to any covalently closed structure. Rings may include, for example, heterocycles (e.g. heteroaryls and non-aromatic heterocycles), aromatics (e.g. aryls and heteroaryls), and non-aromatics (e.g. non-aromatic heterocycles). Rings may be optionally substituted or rings may be fused to at least one ring to form part of a ring system. The term "ring system" refers to two or more rings, wherein two or more of the rings are fused. The term "fused" refers to structures which two or more rings share one or more bonds.

The ring system can be an aromatic or a non-aromatic ring. In some embodiments, the ring system can include 5 to 8 main chain atoms. In other embodiments, the ring system may include 5 or 6 carbon atoms. The ring system can be a fused to at least one 5- to 8-membered ring. As an illustrative example, the ring system may include, but is not limited to pentalene, heptalene, octalene, acenaphthylene, acephenanthrylene, aceanthrylene, triphenylene and acepentalene.

In some embodiments of the compound of formula (I), one or more of the ring atoms in the ring system may be substituted by group X. The group X may include, but is not limited to S, O, N, NH, NHR$^4$, SO or SO$_2$. In other embodiments, one or more of the atoms in the ring system can carry a substituent R. Examples of the substituents of R include, but are not limited to hydrogen, hydroxyl, alkyl, alkylene, alkenyl, alkynyl, acyl, cycloalkyl, cycloalkenyl, substituted or unsubstituted aryl, substituted or unsubstituted heteroaryl, substituted or unsubstituted heteroalicyclyl, halogen, carbonyl, thiocarbonyl, O-carbamyl, O-thiocarbomyl, O-carboxy, isocyanato, thiocyanato, silyl, amino, mono- and di-substituted amino groups, perhaloalkyl, sulfonyl, sulfonamide, thio, —CF$_3$, —CO, —CN, —COOH, —CONH$_2$, —SH, —Se, —SO$_2$, —N=N, —N=O, and OCF$_3$.

The term "alkyl" as used in the present invention refers to a straight or branched chain hydrocarbon group. An alkyl group of this invention may comprise from 1 to 20 carbon atoms. An alkyl group used herein may also be of medium size having 1 to 10 carbon atoms, 1 to 8 carbon atoms, 1 to 5 carbon atoms, 3 to 8 carbon atoms, or 5 to 8 carbon atoms. Examples of alkyl groups include, but are not limited to methyl, ethyl, n-propyl, isopropyl, n-butyl, iso-butyl, sec-butyl, tert-butyl, amyl, tert-amyl, hexyl, octyl, nonyl, decyl, undecyl and dodecyl.

An "alkyl" group of the invention may be substituted or unsubstituted. When substituted, the substituent group(s) is(are) one or more group(s) independently selected from cycloalkyl, aryl, heteroaryl, heteroalicyclyl, hydroxyl, protected hydroxyl, alkoxy, aryloxy, mercapto, alkylthio, arylthio, cyano, halogen, carbonyl, thiocarbonyl, O-carbamyl, O-thiocarbomyl, O-carboxy, isocyanato, thiocyanato, silyl, trihalomethanesulfonyl, and amino.

The term "alkenyl" as used herein refers to an alkyl group that contains in the straight or branched hydrocarbon chain one or more double bonds. An alkenyl group of this invention may be substituted or unsubstituted. When substituted, the substituent(s) may be selected from the same group disclosed above with regard to alkyl group substitution.

The term "alkynyl" as used herein refers to an alkyl group that contains in the straight or branched hydrocarbon chain one or more triple bonds. An alkynyl group of this invention may be substituted or unsubstituted. When substituted, the substituent(s) may be selected from the same group disclosed above with regard to alkyl group substitution.

The term "acyl" as used herein is a group —RC(=O), an acyl group of this invention may be substituted or unsubstituted. When substituted, the substituent(s) may be selected from the same group disclosed above with regard to alkyl group substitution.

As used herein, "cycloalkyl" refers to a completely saturated hydrocarbon ring. Cycloalkyl groups of this invention may range from C$_3$ to C$_8$. A cycloalkyl group of this invention may be substituted or unsubstituted. When substituted, the substituent(s) may be selected from the same group disclosed above with regard to alkyl group substitution.

The term "cycloalkenyl" as used herein refers to a cycloalkyl group that contains one or more double bonds in the ring although, if there is more than one, they cannot form a fully delocalized pi-electron system in the ring (otherwise the group would be "aryl" as defined herein). A cycloalkenyl group of this invention may be substituted or unsubstituted. When substituted, the substituent(s) may be selected from the same group disclosed above with regard to alkyl group substitution.

The term "aryl" as used herein refers to a carbocyclic ring or two or more fused rings that have a fully delocalized pi-electron system. Examples of aryl groups include, but are not limited to benzene, naphthalene and azulene.

As used herein, "heteroaryl" refers to a ring or two, three, four, five, six or more fused rings that contain(s) one or more heteroatoms selected from the group consisting of nitrogen, oxygen, and sulfur in the ring and that have a fully delocalized pi-electron system. Examples of heteroaryl rings include, but are not limited to, aromatic C$_{3-8}$ heterocyclic groups comprising one oxygen or sulfur atom or up to four nitrogen atoms, or a combination of one oxygen or sulfur atom and up to two nitrogen atoms, and their substituted as well as benzo- and pyrido-fused derivatives, for example, connected via one of the ring-forming carbon atoms. Other examples can include furan, thiophene, phthalazinone, pyrrole, oxazole, thiazole, imidazole, pyrazole, isoxazole, isothiazole, triazole, thiadiazole, pyran, pyridine, pyridazine, pyrimidine, pyrazine and triazine.

As used herein, the term "heteroalicyclyl" refers to a ring or one or more fused rings having in the ring system one or more heteroatoms independently selected from nitrogen, oxygen and sulfur. A heteroatom is any atom that differs from carbon. Examples include, but are not limited to N, O, P, S and Se. The rings may also contain one or more double bonds provided that they do not form a fully delocalized pi-electron system in the rings. Heteroalicyclyl groups of this invention may be unsubstituted or substituted. When substituted, the substituent(s) may be one or more groups independently selected from the group consisting of halogen, hydroxyl, protected hydroxyl, cyano, nitro, alkyl, alkoxy, acyl, acyloxy, carboxy, amino and carboxamide.

The term "aromatic" refers to a group comprising a covalently closed planar ring having a delocalized [pi]-electron system comprising 4n+2 [pi] electrons, where n is an integer. Aromatic rings may be formed by five, six, seven, eight, nine, or more than nine atoms. Aromatics may be optionally substituted. Examples of aromatic groups include, but are not limited to phenyl, naphthalenyl, phenanthrenyl, anthracenyl, tetralinyl, fluorenyl, indenyl, and indanyl. The term aromatic includes, for example, benzenoid groups, connected via one of the ring-forming carbon, atoms, and optionally carrying one or more substituents selected from an aryl, a heteroaryl, a cycloalkyl, a non-aromatic heterocycle, a halo, a hydroxy, an amino, a cyano, a nitro, an alkylamido, an acyl, a $C_1$-$C_6$ alkoxy, a $C_1$-$C_6$ alkyl, a $C_1$-$C_6$ aminoalkyl, alkylamino, an alkylsulfenyl, an alkylsulfinyl, an alkylsulfonyl, an sulfamoyl, or a trifluoromethyl. In certain embodiments, an aromatic group is substituted at one or more of the para, meta, and/or ortho positions. Examples of aromatic groups comprising substitutions include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl, 3-cyanophenyl, 4-cyanophenyl, dimethylphenyl, naphthyl, hydroxynaphthyl, hydroxymethylphenyl, (trifluoromethyl)phenyl, alkoxyphenyl, 4-morpholin-4-ylphenyl, 4-pyrrolidin-1-ylphenyl, 4-pyrazolylphenyl, 4-triazolylphenyl, and 4-(2-oxopyrrolidin-1-yl)phenyl.

The term "non-aromatic heterocycle" refers to a group comprising a non-aromatic ring wherein one or more atoms forming the ring is a heteroatom. Non-aromatic heterocyclic rings may be formed by three, four, five, six, seven, eight, nine, or more than nine atoms. Non-aromatic heterocycles may be optionally substituted. In certain embodiments, non-aromatic heterocycles comprise one or more carbonyl or thiocarbonyl groups such as, for example, oxo- and thio-containing groups. Examples of non-aromatic heterocycles include, but are not limited to, lactams, lactones, cyclic imides, cyclic thioimides, cyclic carbamates, tetrahydrothiopyran, 4H-pyran, tetrahydropyran, 1,3-dioxane, 1,4-dioxin, 1,4-dioxane, piperazine, 1,3-oxathiane, 1,4-oxathiane, tetrahydro-1,4-thiazine, 2H-1,2-oxazine, maleimide, succinimide, barbituric acid, thiobarbituric acid, dioxopiperazine, hydantom, dihydrouracil, morphinone, trioxane, hexahydro-1,3,5-triazine, tetrahydrothiophene, tetrahydrofuran, pyrroline, pyrrolidine, pyridone, pyrrohdione, pyrazone, pyrazolidme, imidazoline, imidazolidine, 1,3-dioxole, 1,3-dioxolane, 1,3-dithiole, 1,3-dithiolane, isoxazoline, isoxazolidine, oxazoline, oxazolidine, oxazolidone, thiazoline, thiazolidine, and 1,3-oxathiolane.

The term "heterocycle" refers to a group comprising a covalently closed ring wherein at least one atom forming the ring is a carbon atom and at least one atom forming the ring is a heteroatom. Heterocyclic rings may be formed by three, four, five, six, seven, eight, nine, or more than nine atoms. Any number of those atoms may be heteroatoms (i.e., a heterocyclic ring may comprise one, two, three, four, five, six, seven, eight, nine, or more than nine heteroatoms). Herein, whenever the number of carbon atoms in a heterocycle is indicated (e.g., $C_1$-$C_6$ heterocycle), at least one other atom (the heteroatom) must be present in the ring. Designations such as "$C_1$-$C_6$ heterocycle" refer only to the number of carbon atoms in the ring and do not refer to the total number of atoms in the ring. It is understood that the heterocylic ring will have additional heteroatoms in the ring. In heterocycles comprising two or more heteroatoms, those two or more heteroatoms may be the same or different from one another. Heterocycles may be optionally substituted. Binding to a heterocycle can be at a heteroatom or via a carbon atom. Examples of heterocycles include, but are not limited to the following:

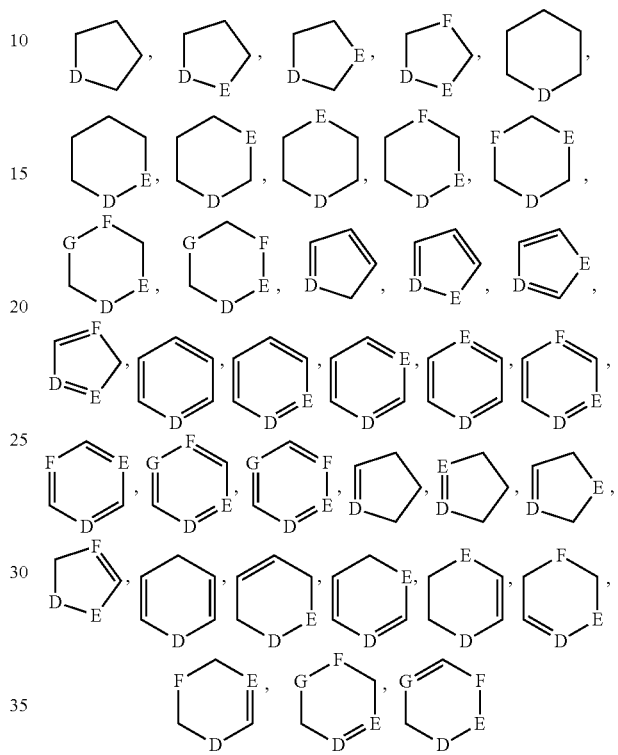

wherein D, E, F, and G independently represent a heteroatom. Each of D, E, F, and G may be the same or different from one another.

The term "heteroatom" refers to an atom other than carbon or hydrogen. Heteroatoms are typically independently selected from oxygen, sulphur, nitrogen, and phosphorus, but are not limited to those atoms. In embodiments in which two or more heteroatoms are present, the two or more heteroatoms may all be the same as one another, or some or all of the two or more heteroatoms may each be different from the others.

The term "optionally substituted" refers to a group in which none, one, or more than one of the hydrogen atoms has been replaced with one or more group(s) are independently selected from: alkyl, heteroalkyl, haloalkyl, heterohaloalkyl, cycloalkyl, aryl, arylalkyl, heteroaryl, non-aromatic heterocycle, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups.

The term "alkoxy", alone or in combination, refers to an aliphatic hydrocarbon having an alkyl-O-moiety. In certain embodiments, alkoxy groups are optionally substituted. Examples of alkoxy groups include, but are not limited to, methoxy, ethoxy, propoxy, butoxy and the like.

, silyl, amino, mono- and di-substituted amino groups, perhaloalkyl, sulfonyl, sulfonamide, thio The term "O-carboxy" refers to a group of formula RC(=O)O.

The term "C-carboxy" refers to a group of formula —C(=O)OR.

The term "acetyl" refers to a group of formula —C(=O)CH$_3$.

The term "trihalomethanesulfonyl" refers to a group of formula X$_3$CS(=O)$_2$— where X is a halogen.

The term "cyano" refers to a group of formula —CN.

The term "isocyanato" refers to a group of formula —NCO.

The term "thiocyanato" refers to a group of formula —CNS.

The term "isothiocyanato" refers to a group of formula —NCS.

The term "S-sulfonamido" refers to a group of formula —S(=O)$_2$NR.

The term "N-sulfonamido" refers to a group of formula RS(=O)$_2$NH—.

The term "O-carbamyl" refers to a group of formula —OC(=O)—NR.

The term "N-carbamyl" refers to a group of formula ROC(=O)NH—.

The term "O-thiocarbamyl" refers to a group of formula —OC(=S)—NR.

The term "N-thiocarbamyl" refers to a group of formula ROC(=S)NH—.

The term "C-amido" refers to a group of formula —C(=O)—NR$_2$.

The term "N-amido" refers to a group of formula RC(=O)NH—.

The term "perhaloalkyl" means alkyl groups in which all the hydrogen atoms are replaced with a halogen atom.

The term "halogen" refers to iodine, bromine, fluorine and chlorine (including any combination of iodine, bromine, fluorine and chlorine.

The terms "amine," and "hydroxy," include such groups that have been esterified or amidified. Procedures and specific groups used to achieve esterification and amidification are known to those of skill in the art.

In some embodiments of the ring system in the compound of formula (I), A and B are electron donating units coordinated to M. A may include, but are not limited to sulfur, nitrogen, oxygen and phosphorus. B is an oxygen or sulfur coordinated to M. M refers to a lanthanide element which includes lanthanum, cerium, neodymium, promethium, europium, gadolinium, terbium, dysprosium, holmium, erbium, thulium and ytterbium.

In other embodiments of the ring system in the compound of formula (I), R is a substituent that can include, but is not limited to hydrogen, hydroxyl, alkyl, alkylene, alkenyl, alkynyl, acyl, cycloalkyl, cycloalkenyl, substituted or unsubstituted aryl, substituted or unsubstituted heteroaryl, substituted or unsubstituted heteroalicyclyl, halogen, carbonyl, thiocarbonyl, O-carbamyl, O-thiocarbomyl, O-carboxy, isocyanato, thiocyanato, silyl, amino, mono- and di-substituted amino groups, perhaloalkyl, sulfonyl, sulfonamide, thio, —CF$_3$, —CO, —CN, —COON, —CONH$_2$, —SH, —Se, —SO$_2$, —N=N, —N=O, and OCF$_3$.

In the compound of formula (I) as defined in the present invention, the ring system C is based on existing compounds that can be obtained by methods known to persons skilled in the art. Examples of the ring system can include, but are not limited to:

2-mercaptopyridine N-oxide (PubChem Compound ID 1570);

2-aminopyridine N-oxide (CAS Number 14150-95-9);

6-mercaptopyridine N-oxide including derivatives thereof (as described in U.S. Pat. No. 4,122,085);

1-oxidopyridin-2-one (PubChem Compound ID 12029945);

1-oxidoquinoline-2-thione (PubChem Compound ID 3082357);

1-oxidoquinoline-2-one (PubChem Compound ID 21139963);

pyridazine-1,2-dioxide (PubChem Compound ID 519643);

3-mercaptopyridazine-2-oxide including derivatives thereof (as described in U.S. Pat. No. 4,041,033);

2-mercaptoquinoxaline-1-oxide (as described in U.S. Pat. No. 3,971,725);

guanine 3-N-oxide (PubChem Compound ID 87841);

hypoxanthine 1-N-oxide (PubChem Compound ID 78847);

3-hydroxyxanthine (PubChem Compound ID 83520);

4-phenylpyrimidin-2-amine 1-oxide (PubChem Compound ID 604485);

adenine N-oxide (as described in Sugiura et. al., *Cancer Research*, (1967), 27 Part 1, 925-931); and 6-mercaptopurine 7-N-oxide as described in Brown et al., *J. Med. Chem.*, 1965, 8 (2), pp 190-195). One or more atoms in any of the ring systems mentioned above can be substituted by the substituent R as described above.

In some embodiments of the compound of the formula (I), L is a complexing moiety, to form a coordinative bond with M. In some embodiments, L can be a solvent in the synthesis of the compound of formula (I). L may have the formula Q-X'-Q', wherein X' binds to M via a coordinative bond.

In the context of the present invention, the term "coordinative bond" or "coordinated" refers to a bond formed between two molecules where one of the species contributes both electrons. Examples of X' that coordinatively binds to M can include, but are not limited to S(O), C(O), C(S), and C(Se). Examples of Q and Q' can independently include, but are not limited to hydrogen, hydroxyl, alkyl, alkenyl, cycloalkyl, cycloalkenyl, substituted or unsubstituted aryl, substituted or unsubstituted heteroaryl, substituted or unsubstituted heteroalicyclyl. Accordingly, illustrative examples of the complexing moiety L of the compound of formula (I) include dimethyl sulfoxide, acetone, thioacetone and propane-2-selone. Q and Q' can be taken together to also form a heteroalicyclyl ring. As an illustrative example, 2-quinolinethiol (CAS Number: 2637-37-8) can be used as a complexing moiety.

In the compound of formula (I) of the invention, m indicates the charge of the compound and includes +1, +2, +3 or +4. Y is an anion, or a combination of anions that balances m.

In one embodiment, an illustrative example of the compound of formula (I) is the compound of formula (Ia):

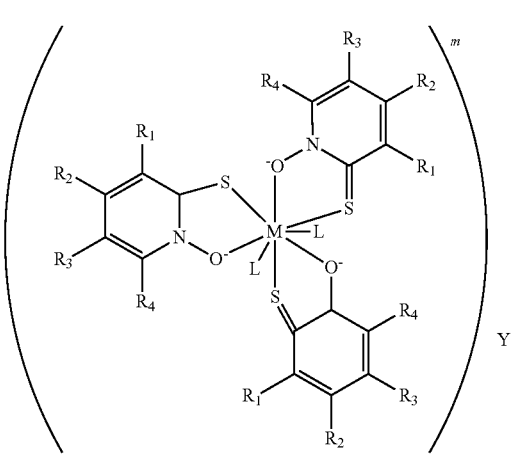

(Ia)

In the compound of formula (Ia), m, M, Y and L have the meaning as defined above in formula (I). $R_1$, $R_2$, $R_3$ and $R_4$ can independently from each other be hydrogen, hydroxyl, alkyl, alkylene, alkenyl, alkynyl, acyl, cycloalkyl, cycloalkenyl, substituted or unsubstituted aryl, substituted or unsubstituted heteroaryl, substituted or unsubstituted heteroalicyclyl, halogen, carbonyl, thiocarbonyl, O-carbamyl, O-thiocarbomyl, O-carboxy, isocyanato, thiocyanato, silyl, amino, mono- and di-substituted amino groups, perhaloalkyl, sulfonyl, sulfonamide, thio, —$CF_3$, —CO, —CN, —COOH, —$CONH_2$, —SH, —Se, —$SO_2$, —N=N, —N=O, and $OCF_3$.

The synthesis of compounds of formula (I) can be carried out as described in Niu et al, *Journal of Chemical Crystallography*, (2004), vol. 34, 195, for example. Generally, to obtain the compound of formula (I), a metal oxide of formula $M_aO_b$ is dissolved under acidic conditions. M is a lanthanide element as defined in formula (I) with "a" being an integer in the range of 1 to 6 and "b" being an integer in the range of 3 to 11. In one embodiment, the integer a can be 1, 2, 3, 4, 5 or 6 and in other embodiments the integer b can be 3, 4, 5, 6, 7, 8, 9, 10 or 11. $M_aO_b$ represents any suitable oxide of a lanthanide element that can be used in the present invention. The formula $M_aO_b$ can include, but are not limited to, lanthanum oxide ($LaO_3$, $La_2O_3$), cerium oxide ($CeO_2$, $Ce_2O_3$), neodymium oxide ($Nd_2O_3$), promethium oxide ($Pm_2O_3$), europium oxide ($Eu_2O_3$), gadolinium oxide ($Gd_2O_3$), terbium oxide ($Tb_2O_3$), dysprosium oxide ($Dy_2O_3$), holmium oxide ($Ho_2O_3$), erbium oxide ($Er_2O_3$), thulium oxide ($Tm_2O_3$) and ytterbium oxide ($Yb_2O_3$). Once the metal oxide such as $M_aO_b$ is dissolved under acidic conditions, the pH of the solution can be increased to a suitable level by adding alkali. Lastly, a solution of the compound of formula (I) can be obtained by adding a compound of the ring system C to the reaction mixture in the presence of a complexing moiety L, where L is defined as above. Illustratively once the solution of the compound of formula (I) is obtained, the crystal compound of formula (I) can be obtained by reducing the temperature of the reaction mixture.

Without wishing to be bound by any theory, it is believed that the compound of formula (I), including samarium (2-mercaptopyridine N-oxide)(dimethyl sulfoxide) and praseodymium (2-mercaptopyridine N-oxide)(dimethyl sulfoxide) are able to modulate the expression of PPARγ transcriptional target proteins in cancer or tumor cells. In this context, it has been demonstrated that PTEN (phosphotase and tensin homologue), MnSOD (manganese superoxide dismutase) RhoB (Ras homolog gene family, member B) act as direct transcriptional targets of PPAR-γ bearing PPRE (PPARγ response element) in their promoter regions (Marlow L A et al, *Cancer Res.*, 69(4), 2009, pp. 1536-1544; Teresi R. E. et al, *Int. J. Cancer*, 118(10), pp. 2390-2398, 2006; and Ding G. et al, *Cardiovasc. Res.*, 76(2), 2007, pp. 269-279). The inventors found that the compound of formula (I), in particular the compound (2-mercaptopyridine N-oxide)(dimethyl sulfoxide) modulates the expression of these target proteins in a manner that corroborates those reported for conventional PPAR-γ ligands such as Rosiglitazone and Ciglitazone. Namely, PTEN and RhoB are upregulated, and MnSOD is downregulated by (2-mercaptopyridine N-oxide)(dimethyl sulfoxide) (FIGS. 14 to 18). Furthermore, real-time PCR results demonstrated that such modulations of the PPARγ transcriptional targets observed at the protein level are also found at the mRNA level, indicating that the compound (2-mercaptopyridine N-oxide)(dimethyl sulfoxide) also regulates these target proteins at the transcriptional level (FIG. 17).

Figure 22:
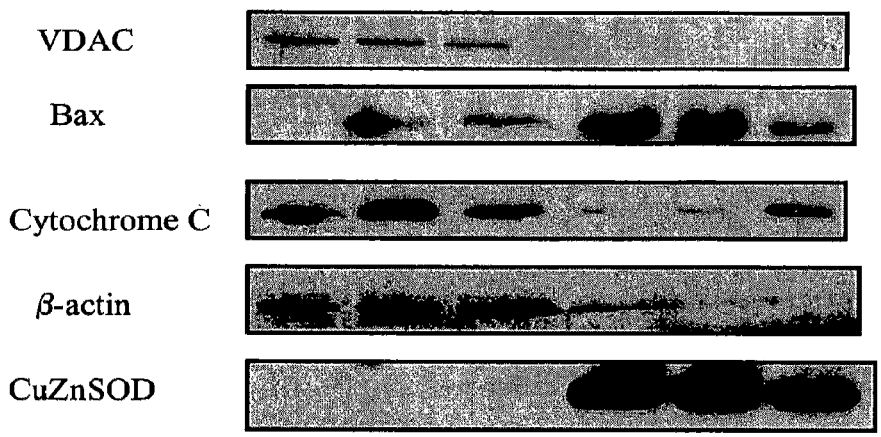
FIG. 22 shows the effect of different concentrations (5 μM and 10 μM) of $C_{19}H_{24}N_3O_5S_5Pr$ (indicated as "Pr-MPO") on SHSY5Y neuroblastoma cells in which Pr-MPO causes Bax translocation to the mitochondrial fraction as well as cytochrome C release into the cytosol after 24 hr treatment. The findings were similar to the findings in FIG. 21.
Figure 23:
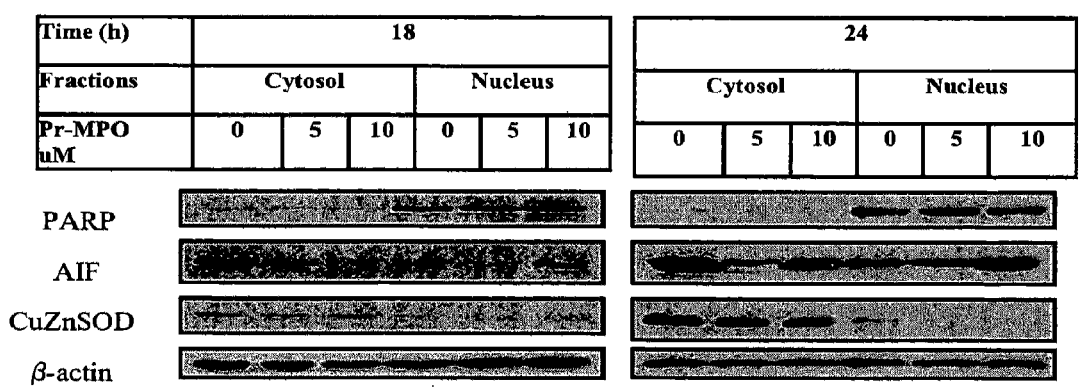
FIG. 23 shows the effect of different concentrations (5 μM and 10 μM) of $C_{19}H_{24}N_3O_5S_5Pr$ (indicated as "Pr-MPO") on the translocation of AIF (Apoptosis Inducing Factor) to the nucleus of SHEP-1 cells after 18 hr and 24 hr treatment. AIF is normally retained in the intermembrane mitochondrial space, where it performs an oxidoreductase function. Upon trigger, AIF is released into the cytosol and then translocated to the nucleus where it is capable of triggering caspase-independent cell death, possibly by causing peripheral chromatin condensation and high molecular weight DNA loss.

In addition, it is also believed by the inventors that despite causing MOMP (mitochondrial outer membrane permeabilization) as evidenced by Bax translocation into the mitochondria and cytochrome C release into cytosol (FIGS. 21 and 22), the compound (2-mercaptopyridine N-oxide)(dimethyl sulfoxide) does not activate caspases in cancer cells. In this context, it was previously reported that the apoptosis inducing factor (AIF) is involved in triggering caspase-independent cell death (Candé et al, *Journal of Cell Science*, 115, 4727-4734 (2002); and Lorenzo H K et al, *Cell Death and Differentiation*, 6, 516-524 (1999). It was thus found by the inventors that AIF was translocated into the nucleus of cancer cells after treatment with the compound (2-mercaptopyridine N-oxide)(dimethyl sulfoxide) (FIG. 23). In addition, the inventors found that the compound (2-mercaptopyridine N-oxide)(dimethyl sulfoxide)induced LC3 II (microtubule-associated protein 1 light chain 3) formation, which is a classical marker of autophagy as described in for example Kabeya Y, *European Molecular Biology Organization Journal*, 19(21), 5720-5728, 2000. Furthermore, preincubation of cancer cells with 3MA (3-methyl adenine), an autophagy inhibitor was able to reverse this formation of LC3-II by Pr-MPO, suggesting that Pr-MPO might be inducing canonical autophagy involving PI3K pathway.

Thus, the present invention also relates to a method of killing a cell, such as a tumor cell, e.g. a cancerous cell or a precancerous cell. The method includes administering a compound of formula (I) or (Ia) as defined above. In some embodiments, the compounds samarium (2-mercaptopyridine N-oxide)(dimethyl sulfoxide) and praseodymium (2-mercaptopyridine N-oxide)(dimethyl sulfoxide) can be used in activating PPARγ and to induce cell killing. Therefore the compound of the present invention can be a PPARγ agonist. In some embodiments, the method is caspase independent.

The present invention also relates to a method of inhibiting, arresting or reversing tumourigenesis in a cell and/or inducing apoptosis in a tumor cell. The method includes administering a compound of formula (I) or (Ia), including the compounds samarium (2-mercaptopyridine N-oxide)(dimethyl sulfoxide) and praseodymium (2-mercaptopyridine N-oxide) (dimethyl sulfoxide).

Any cell may be used in the present method of the invention. In some embodiments, the cell is obtained or derived from a host organism, which may be any organism. The cell may be directly taken, e.g. isolated, from a respective host organism in form of a sample such as e.g. a biopsy or a blood sample. It may also have been obtained, e.g. isolated, from a host organism and subsequently been cultured, grown, transformed or exposed to a selected treatment. In some embodiments, the cell used according to the invention may be comprised in a host organism. It may for instance be present in the blood or in tissue, including in an organ, of the host organism. The host organism from which the cell is derived or obtained, including isolated, purified or enriched, or in which it is included, may be any organism such as a microorganism, an animal, such as a fish, an amphibian, a reptile, a bird, a mammal, including a rodent species, an invertebrate species, e.g. of the subclass Lissamphibia that includes e.g. frogs, toads, salamanders or newts, or a plant. Examples of mammals include, but are not limited to, a rat, a mouse, a rabbit, a squirrel, a vole, a platypus, a chicken, a cow, a goat, a sheep, a pig, a dog, a mouflon, a guinea pig, a hamster, a chimpanzee, a rhesus monkey a macque or a human.

In some embodiments, the cell used in the invention may be a tumor cell, for example a cancer cell. In other embodiments, the tumor may derive from a cancer; A respective tumor cell may also be obtained from an organism, e.g. from a mammal. In other embodiments the tumour cell may be included in a mammal, such as for example a rat, a cow, a pig, and a human. Any tumor or cancer may be used in the invention including for example, a benign tumor and a metastatic malignant tumor. A respective tumor cell may also be cultured. It may for instance be a cell of a cell line, such as, but not limited to, colorectal cancer cell lines SW480, HT29, RKO, LST-R1, Caco-2, WiDr, GP2d, HCT116, LoVo, LS174T, VACO5 HCA7, LS411, C70, LIM1863, SL-174T, SW1417, SW403, SW620, SW837 or VACO4A, melanoma cell lines A375, B16 (including B16-F10), BN1, K1735-M2, M14, OCM-1 or WM793, hepatoma cell lines FHCC-98, H4IIE Hep G2, Hep G2f, Huh-7, PLHC-1, SMMC-7721, SK-Hep1 or QGY, lung cancer cell lines A549, ABC-1, EBC-1, LC-1/sq, LCD, LCOK, LK-2, Lu135, MS-1, NCI-H69, NCI H157, NCI-N231, NL9980, PC1, PC3, PC7, PC9, PC10, PC14, QG56, RERF-LCMS, RERF-LCAI, RERF-LCKJ, SBC3 or SQ5, oesophageal cancer cell lines A549, EC109, EC9706 or HKESC-4, gastric cancer cell lines BGC823, KATO-III, MGC803, MKN-45, SGC7901 or ovarian cancer cell lines A2780, C13*, CAOV3, DOV-13, H08910 (including HO-8910PM), OvCA 3, OvCA 420, OvCA 429, OvCA 432, OvCA 433, OvCar 3, OvCar 5, OvCA 420, OVHM or SKOV-3, breast cancer cell lines MDA-MB-231, T47D, and neuroblastoma cell lines SHSY5Y, SHEP-1. Examples of tumors include, but are not limited to, haematological malignancies and solid tumors. Solid tumors include for instance a sarcoma, arising from connective or supporting tissues, a carcinoma, arising from the body's glandular cells and epithelial cells or a lymphoma, a cancer of lymphatic tissue, such as the lymph nodes, spleen, and thymus. Examples of a solid tumor include, but are not limited to, breast cancer, lung cancer, a brain tumor, a neuroblastoma, colon cancer, rectal cancer, bladder cancer, a liver tumor, a pancreatic tumor, ovarian cancer, prostate cancer and a melanoma.

The term "cancer" refers to any cancer caused by the proliferation of malignant neoplastic cells, such as for instance a tumour, a neoplasm, carcinoma, sarcoma, leukemia, lymphoma. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute nonlymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, a bone tumor and a soft-tissue sarcoma, a common solid tumor of an adult such as head and neck cancer—such as oral, laryngeal, nasopharyngeal and esophageal; genito urinary cancer—such as prostate, bladder, renal, uterine, ovarian, testicular; lung cancer—such as small-cell and non small cell; breast cancer; pancreatic cancer; melanoma and other skin cancers; stomach cancer; a brain tumor; a tumour related to Gorlin's syndrome—such as medulloblastoma or meningioma; and liver cancer. Additional exemplary forms of cancer which may be addressed by a method of the invention include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Some methods and uses according to the invention include or aim at inducing apoptosis in one or more cells involved in a cell proliferative disorder such as hyperplasia, dysplasia and a pre-cancerous lesion. In some embodiments these methods include or aim at inducing apoptosis in a tumor cell. The method includes administering a compound of formula (I) or (Ia) as defined above, including the compounds samarium (2-mercaptopyridine N-oxide)(dimethyl sulfoxide) and praseodymium (2-mercaptopyridine N-oxide)(dimethyl sulfoxide). The method of inducing apoptosis can for example be caspase-independent. In this context, apoptosis is a programmed cell death and typically a mechanism in a multicellular organism to remove undesired cells. Where a cell's capability to undergo or initiate apoptosis is impaired or abolished, a damaged cell is able to proliferate in an unchecked manner, thereby developing into a cancer cell. An apoptotic cell shows a characteristic morphology, by which it can be identified under a microscope. By inducing apoptosis in a tumor cell, a corresponding method may also be used as a therapy for the treatment or prevention of cancer.

In some embodiments, the present invention also relates to a method of treating a mammal having cancer. The method includes administering to the mammal a compound of formula (I) or formula (Ia) as defined above, including the compounds samarium (2-mercaptopyridine N-oxide)(dimethyl sulfoxide) and praseodymium (2-mercaptopyridine N-oxide) (dimethyl sulfoxide). In other embodiments, the present invention provides a method of treating a mammal having diabetes mellitus. The method includes administering to the mammal a compound of formula (I) or formula (Ia) as defined above, samarium (2-mercaptopyridine N-oxide)(dimethyl sulfoxide) and praseodymium (2-mercaptopyridine N-oxide) (dimethyl sulfoxide). Treating" or "treatment" refers to both therapeutic treatment and prophylactic or preventative measures, wherein the object is to prevent, slow down (lessen) or at least partially alleviate or abrogate cancer or diabetes. Those in need of treatment include those already with cancer or diabetes as well as those prone to having the cancer or diabetes those in whom the respective disease is to be prevented (prophylaxis). When the disease is cancer, a subject or mammal is successfully "treated" or shows a reduced tumour burden if, after having undergone a treatment that includes increasing administering the compound of formula (I) or (Ia) according to the present invention, including in some embodiments, the compounds samarium (2-mercaptopyridine N-oxide)(dimethyl sulfoxide) and praseodymium (2-mercaptopyridine N-oxide)(dimethyl sulfoxide), the individual shows observable and/or measurable reduction in, or absence of, one or more of the following: reduction in the number of cancer cells or absence of the cancer cells; reduction in the tumour size; inhibition (i.e., slow to some extent and preferably stop) of cancer cell infiltration into peripheral organs including the spread of cancer into soft tissue and bone; inhibition (i.e., slow to some extent and preferably stop) of tumour metastasis; inhibition, to some extent, of tumour growth; and/or relief to some extent, one or more of the symptoms associated with the specific cancer; reduced morbidity and mortality, and improvement in quality of life issues. To the extent the use or method of the invention may prevent growth and/or kill existing cancer cells, it may be cytostatic and/or cytotoxic. Reduction of these signs or symptoms may also be felt by a respective patient.

The above parameters for assessing successful treatment and improvement in the respective disease are readily measurable by routine procedures familiar to a physician. For cancer therapy, efficacy can be measured, for example, by assessing the time to disease progression (TDP) and/or determining the response rate (RR). Metastasis can be determined by staging tests and by bone scan and tests for calcium level and other enzymes to determine spread to the bone. CT scans can also be done to look for spread to the pelvis and lymph nodes in the area. Chest X-rays and measurement of liver enzyme levels by known methods are used to look for metastasis to the lungs and liver, respectively. Other routine methods for monitoring the disease include transrectal ultrasonography (TRUS) and transrectal needle biopsy (TRNB).

A respective use may for example be the manufacture of a medicament or a pharmaceutical composition for this purpose. Accordingly, the method of the invention includes the use of a compound as defined above, including the use in the manufacture of a medicament. In some embodiments, the invention provides a compound of formula (I) or (Ia) including the compounds samarium (2-mercaptopyridine N-oxide)(dimethyl sulfoxide) and praseodymium (2-mercaptopyridine N-oxide)(dimethyl sulfoxide), or a respective pharmaceutical composition thereof, for treating cancer or diabetes. The term "diabetes" is intended to mean all diabetic conditions, including, without limitation, diabetes mellitus, genetic diabetes, type 1 diabetes, type 2 diabetes, and gestational diabetes. The term "diabetes" also refers to the chronic disease characterized by relative or absolute deficiency of insulin that results in glucose intolerance. Type 1 diabetes is also referred to as insulin dependent diabetes mellitus (IDDM) and also includes, for example, juvenile-onset diabetes mellitus. Type 1 is primarily due to the destruction of pancreatic O-cells. Type 2 diabetes mellitus is also known as non-insulin dependent diabetes mellitus (NIDDM) and is characterized, in part, by impaired insulin release following a meal. Insulin resistance can also be a factor leading to the occurrence of type 2 diabetes mellitus.

Where applicable, a compound of formula (I) or (Ia) may be used in its ionic transition state or any pharmaceutically acceptable salt thereof. A compound of formula I or (Ia) as defined above, or a pharmaceutically acceptable salt thereof, can be used per se, or in a pharmaceutical composition where it may be mixed with other active ingredients, as in combination therapy, and/or a suitable carrier or diluent.

Examples of other active ingredients that may be included in a pharmaceutical composition include, but are not limited to, a nucleic acid alkylator, a nucleoside analogue, an anthracycline, an antibiotic, an aromatase inhibitor, a folate antagonist, an estrogen receptor modulator, an inorganic aresenate, a microtubule inhibitor, a nitrosourea, an osteoclast inhibitor, a platinum containing compound, a retinoid, a topoisomerase 1 inhibitor, a topoisomerase 2 inhibitor, a thymidylate synthase inhibitor, an aromatase inhibitor, a cyclo-oxygenase inhibitor, an isoflavone, a tyrosine kinase inhibitor, a growth factor, a bisphosphonate, and a monoclonal antibody.

Alkylators that may be included in the pharmaceutical composition of the present invention include but are not limited to busulfan (Myleran®, Busilvex®), chlorambucil (Leukeran®), ifosfamide (Mitoxana®, with or without MESNA), cyclophosphamide (Cytoxan®, Neosar®), glufosfamide, melphalan/L-PAM (Alkeran®), dacarbazine (DTIC-Dome®), and temozolamide (Temodar®). As an illustrative example, the compound 2-bis[(2-chloroethyl)amino]tetrahydro-2H-1,3,2-oxazaphosphorine, 2-oxide, also commonly known as cyclophosphamide, is an alkylator used in the treatment of stages III and IV malignant lymphomas, multiple myeloma, leukemia, mycosis fungoides, neuroblastoma, ovarian adenocarcinoma, retinoblastoma, and carcinoma of the breast.

Nucleoside analogues that may be included in the pharmaceutical composition of the present invention include, but are not limited to, cytarabine (Cytosar®) and gemcitabine (Gemzar®), two fluorinated deoxycytidine analogues, fludarabine (Fludara®), a purine analog, 6-mercaptopurine (Puri-Nethol®) and its prodrug azathioprine (Imuran®).

Anthracyclines that may be included in the pharmaceutical composition of the present invention include, but are not limited to, doxorubicin (Adriamycin®, Doxil®, Rubex®), mitoxantrone (Novantrone®), idarubicin (Idamycin®), valrubicin (Valstar®), and epirubicin (Ellence®). As one example the compound (8S,10S)-10-(4-amino-5-hydroxy-6-methyl-tetrahydro-2H-pyran-2-yloxy)-6,8,11-trihydroxy-8-(2-hydroxyacetyl)-1-methoxy-7,8,9,10-tetrahydrotetracene-5,12-dione, more commonly known as doxorubicin, is a cytotoxic anthracycline antibiotic isolated from cultures of *Streptomyces peucetius* var. *caesius*. Doxorubicin has been used successfully to produce regression in disseminated neoplastic conditions such as acute lymphoblastic leukemia, acute myeloblastic leukemia, Wilm's tumor, neuroblastoma, soft tissue and bone sarcomas, breast carcinoma, ovarian carcinoma, transitional cell bladder carcinoma, thyroid carcinoma, lymphomas of both Hodgkin and non-Hodgkin types, bronchogenic carcinoma, and gastric carcinoma.

Antibiotics that may be included in the pharmaceutical composition of the present invention include but are not limited to dactinomycin, actinomycin D (Cosmegen®), daunorubicin/daunomycin (Cerubidine®, DanuoXome®), bleomycin (Blenoxane®), epirubicin (Pharmorubicin®) and mitoxantrone (Novantrone®). Aromatase inhibitors useful in the practice of the present invention include but are not limited to anastrozole (Arimidex®) and letroazole (Femara®). Bisphosphonate inhibitors that may be included in the pharmaceutical composition of the present invention include but are not limited to zoledronate (Zometa®).

Cyclooxygenase inhibitors that may be included in the pharmaceutical composition of the present invention include but are not limited to acetylsalicylic acid (Aspirin®), celecoxib (Celebrex®) and rofecoxib (Vioxx®, Ceoxx®, Ceeoxx®). Estrogen receptor modulators that may be included in the composition of the present invention include but are not limited to tamoxifen (Nolvadex®) and fulvestrant (Faslodex®). Folate antagonists that may be included in the composition of the present invention include but are not limited to methotrexate (Trexall®, Rheumatrex®) and trimetrexate (Neutrexin®). As an illustrative example, the compound (S)-2-(4-(((2,4-diaminopteridin-6-yl)methyl)methylamino)benzamido)pentanedioic acid, commonly known as methotrexate, is an antifolate drug that has been used in the treatment of gestational choriocarcinoma and in the treatment of patients with chorioadenoma destruens and hydatiform mole. It is also useful in the treatment of advanced stages of malignant lymphoma and in the treatment of advanced cases of mycosis fungoides.

Inorganic arsenates that may be included in the pharmaceutical composition of the present invention include but are not limited to arsenic trioxide (Trisenox®). Microtubule inhibitors (as used herein, a "microtubule inhibitor" is any agent that interferes with the assembly or disassembly of microtubules) that may be included in the composition of the present invention include but are not limited to vincristine (Oncovin®), vinblastine (Velban®), paclitaxel (Taxol®, Paxene®), vinorelbine (Navelbine®), docetaxel (Taxotere®), epothilone B or D or a derivative of either, and discodermolide or its derivatives.

Nitrosoureas that may be included in the pharmaceutical composition of the present invention include but are not limited to procarbazine (Matulane®), lomustine (CeeNU®), carmustine (BCNU®, BiCNU®, Gliadel Wafer®), and estramustine (Emcyt®). Nucleoside analogs that may be included in the pharmaceutical composition of the present invention include but are not limited to 6-mercaptopurine (Purinethol®), 5-cytarabine (Cytosar-U®, DepoCyt®), floxuridine (FUDR®), fludarabine (Fludara®), pentostatin (Nipent®), cladribine (Leustatin®, 2-CdA®), gemcitabine (Gemzar®), and capecitabine (Xeloda®). As an illustrative example, the compound 5-fluoro-2,4(1H,3H)-pyrimidinedione, also commonly known as 5-fluorouracil, is an antimetabolite nucleoside analogue effective in the palliative management of carcinoma of the colon, rectum, breast, stomach, and pancreas in patients who are considered incurable by surgical or other means. Another example of a nucleoside analogue is Gemcitabine. Gemcitabine is 2'-deoxy-2',2'-difluoro-cytidine. It is commercially available as the monohydrochloride salt, and as the beta-isomer. It is also known chemically as 1-(4-amino-2-oxo-1-H-pyrimidin-1-yl)-2-desoxy-2,2-difluororibose.

An illustrative example of an osteoclast inhibitor that may be included in the pharmaceutical composition of the present invention is pamidronate (Aredia®). Platinum compounds that may be included in the pharmaceutical composition of the present invention include, but are not limited to, cisplatin (Platinol®) and carboplatin (Paraplatin®). Retinoids that may be included in the pharmaceutical composition of the present invention include but are not limited to tretinoin, ATRA (Vesanoid®), alitretinoin (Panretin®), and bexarotene (Targretin®). Topoisomerase 1 inhibitors that may be included in the pharmaceutical composition of the present invention include, but are not limited to, topotecan (Hycamtin®) and irinotecan (Camptostar®, Camptothecan-11®). Topoisomerase 2 inhibitors that may be included in the pharmaceutical composition of the present invention include, but are not limited to, etoposide (Etopophos®, Vepesid®) and teniposide (Vumon®).

Examples of a tyrosine kinase inhibitors that may be included in the pharmaceutical composition of the present invention include, but are not limited to, dasatinib (Sprycel®), erlotinib (Tarceva®), gefitinib (Iressa®), imatinib (Gleevec®), lapatinib (Tykerb®), sorafenib (Nexavar®) and vandetanib (Zactima®). Examples of a (recombinant) growth factor that may be included in the pharmaceutical composition of the present invention include, but are not limited to, interleukin-11, interferon-α-2b and interleukin-2.

An illustrative example of a thymidylate synthase inhibitor that may be included in the pharmaceutical composition of the present invention is Raltitrexed®. Examples of a monoclonal antibody that may be included in the pharmaceutical composition of the present invention include, but are not limited to, rituximab (MabThera®) or cetuximab (Erbitux®).

In some embodiments, the pharmaceutical composition includes the compounds samarium (2-mercaptopyridine N-oxide)(dimethyl sulfoxide) and praseodymium (2-mercaptopyridine N-oxide)(dimethyl sulfoxide). The pharmaceutical composition can be used as a PPARγ agonist. Therefore, the pharmaceutical composition may include the compound praseodymium(2-mercaptopyridine N-oxide)(dimethyl sulfoxide).

The present invention also relates to a method of treating a mammal having cancer or diabetes comprising administering to the mammal the pharmaceutical composition as defined above.

A pharmaceutical composition according to the present invention may be administered by, for example, the oral, topical, dermal, ocular, intravenous, intraarticular, rectal, vaginal, inhalation, intranasal, sublingual or buccal route. Accordingly, the present invention also provides administering to an organism, such as a cell or a mammal, a compound of the general formula (I) (see above), including a composition that includes a respective compound. Any cell may be used in the present method of the invention. As an illustrative example, a tumor cell may be used. Examples of suitable mammals include, but are not limited to, a rat, a cow, a goat, a sheep, a pig, a dog, a mouflon, a guinea pig, a hamster, a chimpanzee, a rhesus monkey and a human.

The term "administering" relates to a method of incorporating a compound or pharmaceutical composition according of the invention including the compounds samarium (2-mercaptopyridine N-oxide)(dimethyl sulfoxide) and praseodymium (2-mercaptopyridine N-oxide)(dimethyl sulfoxide) into one or more cells or tissues of an organism. Exemplary routes of administration of a respective compound or pharmaceutical composition include oral, transdermal, and parenteral delivery (see also above). Suitable routes of administration may, for example, include depot, oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections. One may also administer the compound or pharmaceutical composition in a local rather than systemic manner, for example, via injection of the compound directly into a solid tumor, such as in a depot or sustained release formulation. Furthermore, a respective compound or pharmaceutical composition may be used in a targeted drug delivery system, for example, in a liposome coated with a tumor-specific antibody. Such liposomes may for example be targeted to and taken up selectively by a tumor.

The invention also provides a method of modulating the expression of a PPAR-γ target protein in a cell, for example a tumor or cancer cell as described above. The method includes contacting the cell with a compound of formula (I), including the compounds samarium (2-mercaptopyridine N-oxide) (dimethyl sulfoxide) and praseodymium (2-mercaptopyridine N-oxide)(dimethyl sulfoxide). In this context, the modulating can for example include modulating the expression of the PPAR-γ target at the gene or protein level. Some of these methods are in vivo or in vitro methods In this context, a gene expression level or an amount of a protein level is deemed to be "altered" or "modulated" when the gene expression/activity/amount of the respective protein is increased or decreased by about 10%, about 25%, about 50%, about 75%, about 100%, or higher, as compared to the control level. Alternatively, an expression level or an activity level or a protein level/amount is deemed "increased" or "decreased" when gene expression/or an activity/protein level is increased or decreased by at least about 0.1, at least about 0.2, at least about 1, at least about 2, at least about 5, or at least about 10 or more fold as compared to a control level.

The PPAR-γ target protein used herein can be one of phosphotase and tensin homologue (PTEN), manganese superoxide dismutase (MnSOD) and Ras homolog gene family, member B (RhoB). In some embodiments, the amount of PTEN and RhoB are increased in the cell. In other embodiments, the amount of MnSOD is decreased in the cell.

Based on the inventors' finding the invention also provides methods of identifying a candidate compound that is capable of preventing, inhibiting, arresting or reversing tumorigenesis, including carcinogenesis, in a cell and/or of inducing apoptosis in a tumor cell. The method includes introducing the compound into a cell capable of expressing a PPAR-γ target protein. The method further includes determining the expression of the PPAR-γ target protein wherein an altered/modulated expression of the PPAR-γ target protein is an indication that the compound is capable of preventing, inhibiting, arresting or reversing tumourigenesis in a cell and/or inducing apoptosis in a tumor cell. Some of these methods are in vivo or ex vivo methods. Some of the methods are in-vitro methods of identifying a respective compound.

The present methods of the invention may furthermore include comparing the results of measuring the expression of the PPAR-γ target protein with results of a control measurement (or "reference" measurement). The control measurement may include the use of conditions that do not alter/modulate the expression of the PPAR-γ target protein. In comparing expression, detected levels may for example be compared to a control level. The term "control level" as used herein refers to the number of molecules of the respective protein, e.g. in a cell, a mRNA or protein expression level of a PPAR-γ target protein in a control sample. The term thus includes both a normal control level and a cancer control level (see also below). The term can refer to a single reference measurement or to a plurality of reference measurements. In some embodiments the control level may be a database of expression or activity values from previously conducted measurements.

The invention further provides a method of identifying a candidate compound capable of activating a PPAR-γ receptor protein in a cell. The method comprising introducing the compound into a cell expressing PTEN, MnSOD and RhoB, and determining the expression of PTEN, MnSOD and RhoB, wherein an increased expression of PTEN and RhoB and a decreased expression of RhoB is an indication that the compound is capable of activating the PPAR-γ receptor protein.

In order that the invention may be readily understood and put into practical effect, particular embodiments will now be described by way of the following non-limiting examples.

EXAMPLES

Cell Culture and Culture Conditions

The T47D and MDA-MB-231 breast cancer cell lines and SHSY5Y neuroblastoma cell lines were obtained from the American Type Culture Collection (ATCC) VA, USA. SHEP 1 neuroblastoma cells were provided as a gift from Dr. Eva L Feldman, Director of the Neuropathy Center, University of Michigan Health System, Ann Arbor, Mich. USA. These cell lines were propagated and maintained in culture in RPMI medium (Hyclone), supplemented with 10% fetal bovine serum (FBS: Hyclone Logan, Utah, USA), 2 mM L-glutamine (Hyclone), and 1 mM gentamicin sulphate (Bio-Whittaker) in a humidified incubator at 37° C. and 5% $CO_2$. SHEP1 cells were propagated and maintained in DMEM medium (Hyclone) containing 10% fetal bovine serum (FBS), 0.12% HEPES, 0.17% sodium bicarbonate, 2 mM L-glutamine (Hyclone), and 1 mM gentamicin sulfate (Bio-Whittaker) at 37° C. and 5% $CO_2$. Cultures were replenished with fresh medium every 2 to 3 days and split 1:3 when they reached 80% confluence.

Western Blotting

Whole cell lysates were prepared with RIPA lysis buffer containing 10 mM Tris-HCL pH7.4, 30 mM NaCl, 1 mM EDTA, 1% Nonidet P-40, supplemented with 1 mM $Na_3VO_4$, 1 µg/ml leupeptin, 1 µg/ml pepstatin A, 1 µg/ml aprotinin and 1 mM PMSF before use. Protein concentration was determined for each sample and equal amounts of protein were boiled for 5 min for other proteins, with 1×SDS sample buffer and resolved by 8% SDS-PAGE. Thereafter, proteins were transferred onto nitrocellulose membrane, blocked for 1 h at room temperature with 5% non-fat milk, and incubated overnight at 4° C. with the primary antibody. After probing with secondary antibody for 1 hr at 25° C., protein bands were detected by using the Supersignal West Pico Chemiluminescence (Pierce). β-actin antibody was used as a loading control.

Mouse anti-β-actin monoclonal antibody was supplied by Sigma-Aldrich, USA. Mouse anti-HuPPARγ E8 monoclonal antibody was purchased from Santa Cruz, USA. Rabbit Anti-PPAR gamma, phospho (Ser82) monoclonal antibody was purchased from Millipore, USA. Stabilized goat anti-mouse horseradish peroxidase (HRP) and goat anti-rabbit horseradish peroxidase (HRP) were obtained from Pierce, USA. The specific primary antibodies used for detecting PTEN, NHE1, RhoB, MnSOD, Bcl2, VDAC, CuZnSOD, LC3I and LC3II were supplied by Cell Signaling Technology, Inc, USA. The specific primary antibodies used for detecting Bax and Cytochrome were supplied by Santa Cruz Biotechnology, Inc, USA.

Example 1

Preparation of $C_{19}H_{24}N_3O_5S_5Pr$ Compound

The present example illustrates the preparation of a compound of the formula $C_{19}H_{24}N_3O_5S_5Pr$ (Refer to FIG. 1). Information of the synthesis of this compound is provided by Niu et al, *Journal of Chemical Crystallography*, (2004), vol. 34, 195. The starting materials, Praesodymium oxide ($Pr_6O_{11}$) for instance, is purchased from Sigma Aldrich Pte Ltd (CAS Number: 12037-29-05). In a small flask, $Pr_6O_{11}$ (102.1 mg, 0.1 mmol) was dissolved in HCl (6M, 10 ml). The solution was neutralized with a solution of NaOH (1M) to pH=5. A solution of 2-mercaptopyridine N-oxide sodium salt (282.3 mg, 1.8 mmol, 95% active) in water was added in the presence of dimethyl sulfoxide (DMSO). The solution was stirred for either 2 hours at 40° C. in the absence of light, or for 1 hr at 40° C., so long as the compound was fully dissolved. The solution was then cooled to room temperature to give green microcrystals, which were collected by filtration, washed successively with $H_2O$ EtOH and dried in vacuo. Pale green prism crystals suitable for X-ray analysis were obtained by recrystallization of the precipitate from DMSO. Fine green crystals of the $C_{19}H_{24}N_3O_5S_5Pr$ compound were obtained after 4 to 7 weeks at 4° C.

$C_{19}H_{24}N_3O_5S_5Pr$: (Found: C, 33.81; H, 3.62; N, 6.28%. Calc. for $C_{19}H_{24}N_3O_5S_5Pr$: C, 33.78; H, 3.58; N, 6.22%); IR (cm⁻1): 1141 (s, CS), 1090 (s, NO); UV-vis (DMSO): 290, 346 nm.

Example 2

Detection of PPARγ Activity Upon Exposure to $C_{19}H_{24}N_3O_5S_5Pr$ Compound and 15d-PGJ$_2$ To determine if $C_{19}H_{24}N_3O_5S_5Pr$ activates PPARγ, SHSY5Y and SHEP1 neuroblastoma cells were transiently co-transfected with a 3×PPRE luciferase plasmid and renilla plasmid for transfection efficiency. Forty eight hours following transfection, the cells were exposed to increased concentrations (0 to 10 μM) of 15d-PGJ$_2$ and $C_{19}H_{24}N_3O_5S_5Pr$ for 18 hours. The fold increase in luciferase activity correlates with the PPARγ activity of the cell. PPARγ activity is determined by calculating the RLU/renilla/μg total protein.

Figure 2A:
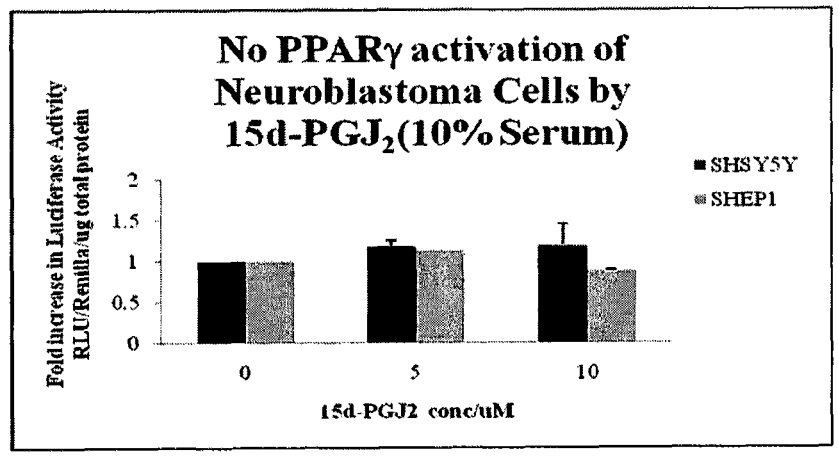
FIG. 2 depicts the detection of PPARγ activation in neuroblastoma cells (SHSY5Y and SHEP1 neuroblastoma cells) upon exposure to endogenous PPARγ ligand 15-deoxy-Delta-12,14, prostaglandin ("15d-PGJ$_2$") (see FIG. 2A) and $C_{19}H_{24}N_3O_5S_5Pr$ ("Pr") obtained in Example 1 (see FIG. 2B) as described in Example 2. The neuroblastoma cells are SHSY5Y (black box) and SHEP1 (grey box). SHSY5Y and SHEP1 neuroblastoma cells were transiently co-transfected with a 3×PPRE luciferase plasmid and renilla plasmid. Forty eight hours following transfection, the neuroblastoma cells were exposed to 15d-PGJ$_2$ and $C_{19}H_{24}N_3O_5S_5Pr$ at increased concentrations (0 to 10 µM) for 18 hours. PPARγ activation was determined by measuring the luciferase activity calculated as luciferase RLU/renilla/µg total protein.
Figure 2B:
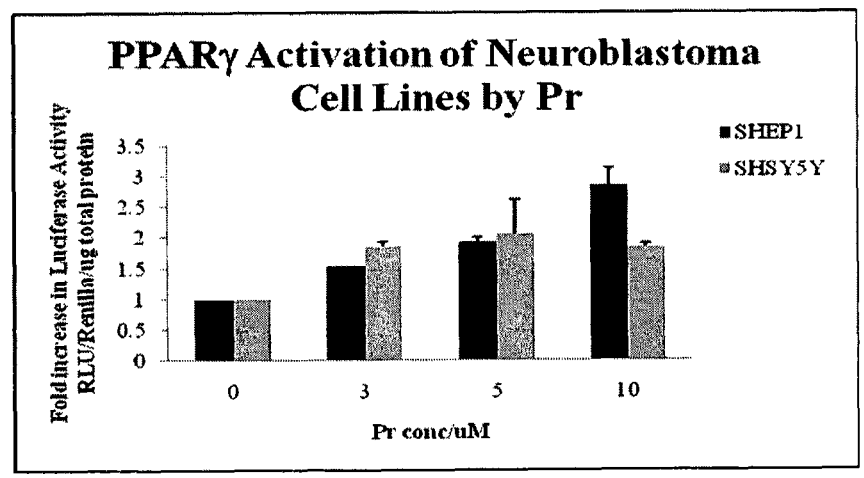

Referring to FIG. 2A, neuroblastoma cells cultured in 10% serum did not display any PPARγ activation when exposed to various doses of 15dPGJ2. However, it can be seen from FIG. 2B that these cells cultured in the same medium condition showed significant activation of PPARγ when exposed to varying doses of $C_{19}H_{24}N_3O_5S_5P$.

Example 3

$C_{19}H_{24}N_3O_5S_5Pr$ Activates PPAR-γ in Breast Cancer Cell Lines

To determine if $C_{19}H_{24}N_3O_5S_5Pr$ activation of PPARγ is dependent on expression of PPARγ in breast cancer cells, breast cancer cells MDA-MB-231 and T47D were transiently co-transfected with a 3×PPRE luciferase plasmid and renilla plasmid for transfection efficiency. Forty eight hours following transfection, cells were exposed to increased concentrations (0 to 20 μM) of $C_{19}H_{24}N_3O_5S_5Pr$ for 18 hours. PPARγ activity was calculated as luciferase RLU/renilla/μg total protein.

Figure 3A:
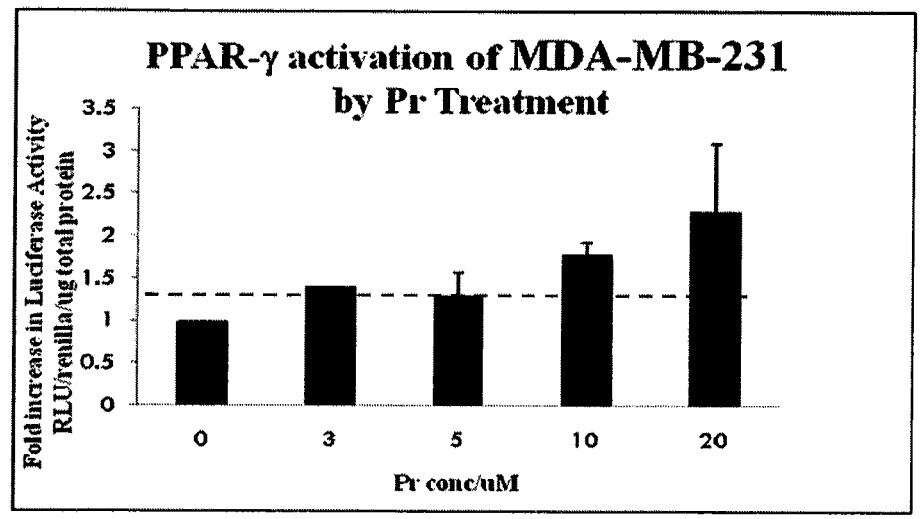
FIG. 3 depicts the detection of PPARγ activation in two breast cancer cell lines upon exposure to $C_{19}H_{24}N_3O_5S_5Pr$ ("Pr treatment") as described in Example 3. The breast cancer cell lines are MDA-MB-231 (FIG. 3A) and T47D (FIG. 3B). The cells were transiently co-transfected with a 3×PPRE luciferase plasmid and renilla plasmid. Forty eight hours following transfection, MDA-MB-231 cells were exposed to $C_{19}H_{24}N_3O_5S_5Pr$ (Pr) at increased concentrations (0 to 20 µM) for 18 hours. T47D cells were also exposed to $C_{19}H_{24}N_3O_5S_5Pr$ (Pr) at increasing concentrations (0 to 10 µM) for 18 hours. PPARγ activation was determined by measuring the luciferase activity as calculated as luciferase RLU/renilla/µg total protein.
Figure 3B:
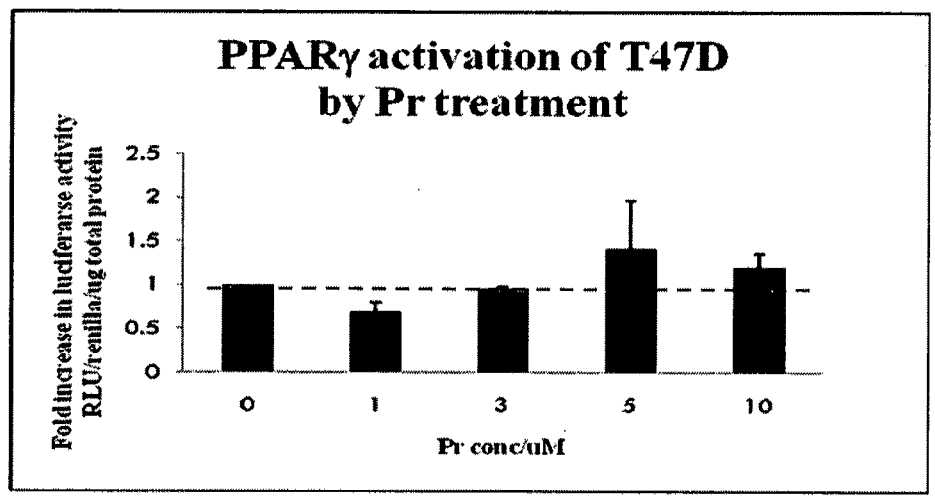
Figure 4:
FIG. 4 depicts the results of a Western blot analysis, showing the expression of PPARγ in MDA-MB-231 and T47D cells (upper panel). The expression of β-actin in both MDA-MB-231 and T47D cells (lower panel) confirmed equivalent total protein blotting. Forty eight hours following transfection, cells were exposed to various concentrations of Pr for 18 h. PPARγ activity was calculated as luciferase RLU/renilla/µg total protein. Cell viability was assessed by MTT assay as described in Example 4 and in FIG. 5.

It is seen from FIG. 3 that $C_{19}H_{24}N_3O_5S_5Pr$ activates PPARγ better in MDA-MB-231 cells, than in T47D cells. MDA-MB-231 cells have a higher PPARγ expression, compared to T47D cells, as illustrated in FIG. 4.

Example 4

Detection of Breast Cancer Cell Death Via Cell Viability Assay

To detect breast cancer cell death via cell viability assay, the mitochondrial activity, as an index of cell viability, was measured using the MTT method (Mosmann, T. *J Immunol Methods*, 1983; 65: 55-63). Briefly, cells were treated in triplicates in 96-well plate. After completion of the experimental period, 20 μl of MTT reagent (5 mg/ml) was added per well of culture (containing 100 μl treatment media). The reaction was allowed to proceed for 4 to 6 h at 37° C. SDS (10%) was then added (200 μl/well) overnight and the absorption at 595 nm measured.

Figure 5:
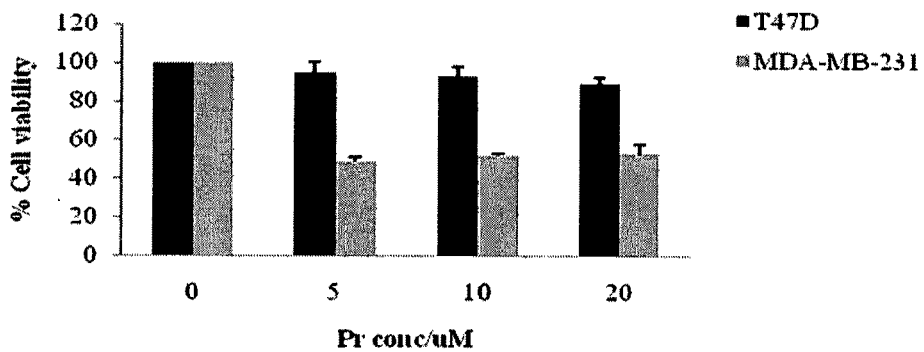
FIG. 5 depicts the cell viability of T47D breast cancer cells (black box) and MDA-MB-231 breast cancer cells (grey box) after exposure to $C_{19}H_{24}N_3O_5S_5Pr$ ("Pr treatment") for 24 hours. Cell viability was assessed by MTT assay as described in Example 4.

Data from FIG. 5 shows that the degree of activation of PPARγ corroborates with the ability of $C_{19}H_{24}N_3O_5S_5Pr$ to induce cell death. $C_{19}H_{24}N_3O_5S_5Pr$ inhibits growth of high PPARγ expressing cells (MDA-MB-231) while low PPARγ expressing cells (T47D) remained viable.

Example 5

$C_{19}H_{24}N_3O_5S_5Pr$ Activates PPAR-γ in Neuroblastoma Cancer Cell Lines To assess if $C_{19}H_{24}N_3O_5S_5Pr$ activation of PPARγ is dependent on expression of PPARγ neuroblastoma cells, neuroblastoma cells SHEP1 and SHSY5Y were transiently co-transfected with a 3×PPRE luciferase plasmid and renilla plasmid for transfection efficiency. Forty eight hours following transfection, cells were exposed to increased concentrations (0 to 20 μM) of $C_{19}H_{24}N_3O_5S_5Pr$ for 18 hours. PPARγ activity was calculated as luciferase RLU/renilla/μg total protein.

Figure 6A:
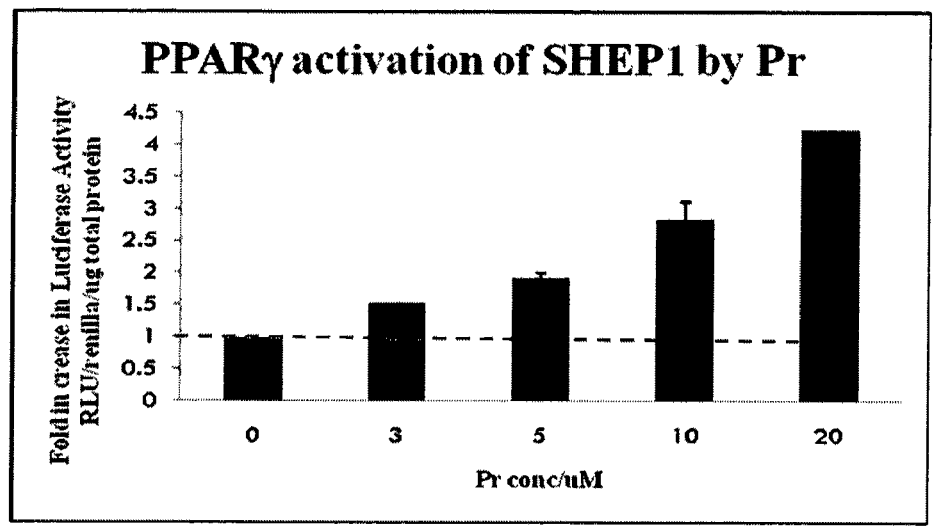
FIG. 6 depicts the detection of PPARγ activation in neuroblastoma cells SHEP1 (FIG. 6A) and SHSY5Y (FIG. 6B). The cells were transiently co-transfected with a 3×PPRE luciferase plasmid and renilla plasmid. Forty eight hours following transfection, SHEP1 cells were exposed to $C_{19}H_{24}N_3O_5S_5Pr$ (Pr) at increased concentrations (0 to 20 µM) for 18 hours. SHSY5Y cells were exposed to $C_{19}H_{24}N_3O_5S_5Pr$ (Pr) at increased concentrations (0 to 10 µM) for 18 hours. PPARγ activity was calculated as luciferase RLU/renilla/µg total protein.
Figure 6B:
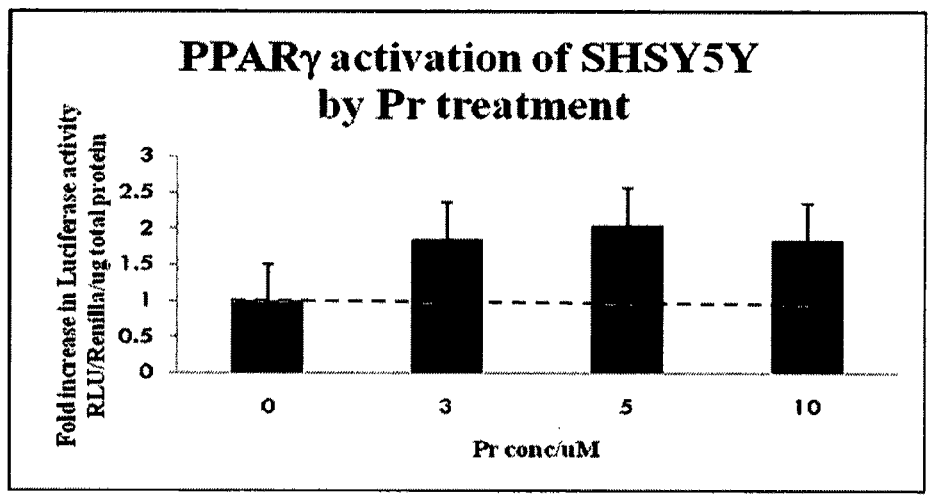
Figure 7:
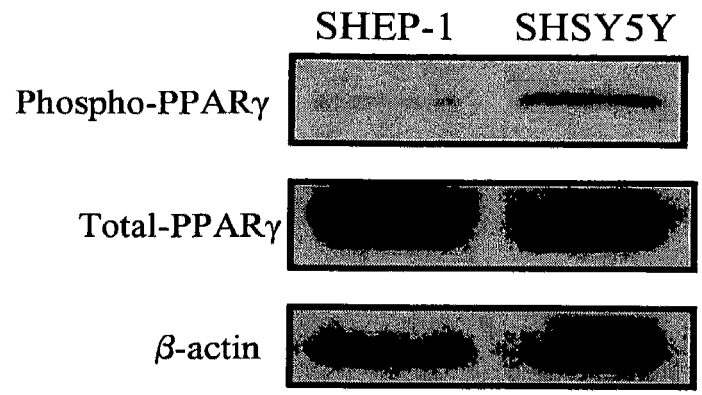
FIG. 7 depicts the results of a Western blot analysis, showing the expression of phosphorylated PPARγ in SHEP-1 and SHSY5Y neuroblastoma cells (top panel, "Phospho-PPARγ"). The total amount of PPARγ expressed in both SHEP-1 and SHSY5Y cells are shown in the middle panel ("Total-PPARγ"). The expression of β-actin in both SHEP-1 and SHSY5Y cells (lower panel, "β-actin") confirmed equivalent total protein blotting.

Data obtained from FIG. 6 shows that $C_{19}H_{24}N_3O_5S_5Pr$ activates PPARγ better in SHEP1 cells, than in SHSY5Y cells. SHEP1 cells have a higher PPARγ activity as indicated by the presence of lower phosphorylated PPARγ, illustrated in FIG. 7. SHSY5Y cells have reduced PPARγ activity due to the presence of phosphorylated PPARγ as illustrated in FIG. 7.

Example 6

Detection of Neuroblastoma Cell Death Via Cell Viability Assay

The cell viability assay of SHEP 1 and SHSY5Y cells was performed using the same method as described in Example 4.

Figure 8:
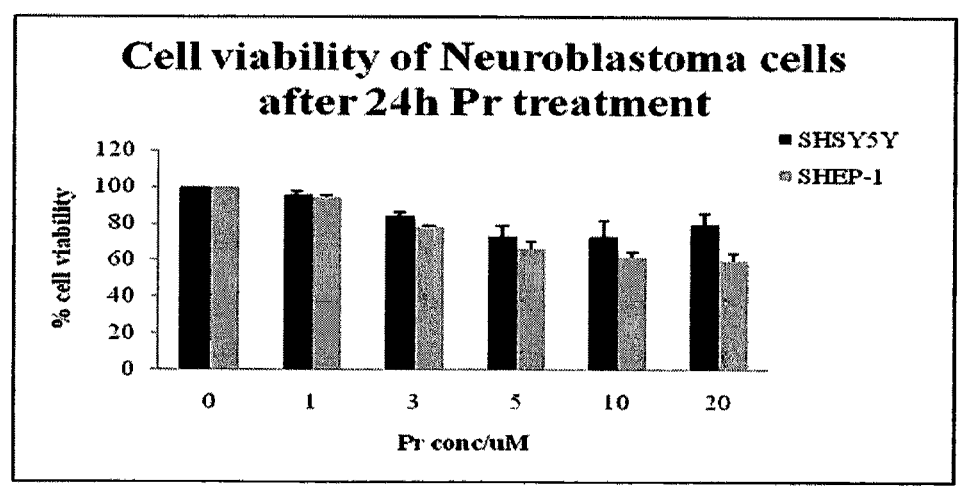
FIG. 8 depicts the cell viability of SHSY5Y neuroblastoma cells (black box) and SHEP-1 neuroblastoma cells (grey box) after exposure to $C_{19}H_{24}N_3O_5S_5Pr$ (Pr) for 24 hours. Cell viability was assessed by MTT assay as described in Example 4.

Data obtained from FIG. 8 shows the degree of activation of PPARγ corroborates with the ability of $C_{19}H_{24}N_3O_5S_5Pr$ to induce cell death. $C_{19}H_{24}N_3O_5S_5Pr$ has a greater growth of SHEP1 cells compared to SHSY5Y cells.

Example 7

Overexpression of Phosphorylation-Defective PPARγ in SHSY5Y Cells

Since PPARγ in SHSY5Y cells are highly phosphorylated, the following experiment is performed to determine if $C_{19}H_{24}N_3O_5S_5Pr$ could activate a phosphorylation defective mutant PPARγ in SHSY5Y cells.

SHSY5Y neuroblastoma cells were transiently co-transfected with either a plasmid encoding wild type PPARγ or a phosphorylation-defective mutant of PPARγ (GFP-PPARg S82A), 3×PPRE luciferase plasmid and plasmid encoding renilla for transfection efficiency. Forty eight hours following transfection, cells were exposed to 10 uM of $C_{19}H_{24}N_3O_5S_5Pr$ for 18 hours. PPARγ activity was calculated as luciferase RLU/renilla/μg total protein.

Figure 9:
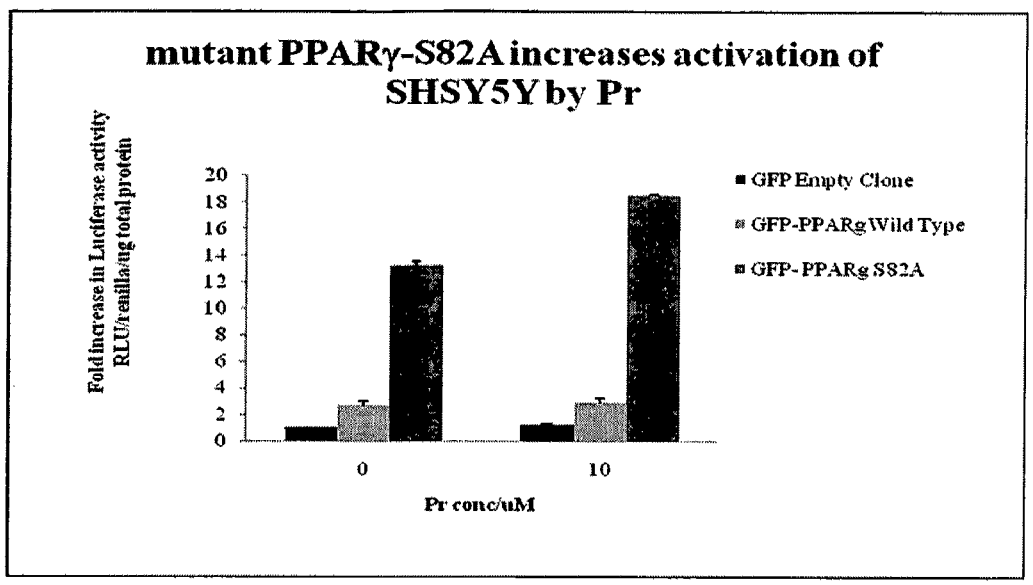
FIG. 9 illustrates the PPARγ activation of a phosphorylation-defective mutant form of PPARγ in SHSY5Y neuroblastoma cells (indicated as "GFP-PPARg S82A") upon exposure to $C_{19}H_{24}N_3O_5S_5Pr$ (Pr) as described in Example 7. "GFP-PPARg Wild Type" refers to SHSY5Y neuroblastoma cells that were transfected with a plasmid encoding wild type PPARgamma (GFP-PPARg Wild Type). "GFP empty clone" is a negative control and refers to SHSY5Y neuroblastoma cells transfected with an empty vector. PPARγ activity was calculated as luciferase RLU/renilla/μg total protein.

FIG. 9 shows a significant activation of phosphorylation-defective mutant PPARγ in SHSY5Y cells compared to wild type PPARγ.

Example 8

Overexpression of Wildtype PPARγ in SHEP1 Cells Increases Anti-Proliferative Effect of $C_{19}H_{24}N_3O_5S_5Pr$ To determine if $C_{19}H_{24}N_3O_5S_5Pr$-induced PPARγ activation is responsible for cell death in neuroblastoma SHEP1 cells, SHEP1 cells were transiently transfected with either empty vector or a vector encoding wild type PPARγ. Forty eight hours following transfection, cells were exposed to increased concentrations (0 to 5 uM) of $C_{19}H_{24}N_3O_5S_5Pr$.

Figure 10:
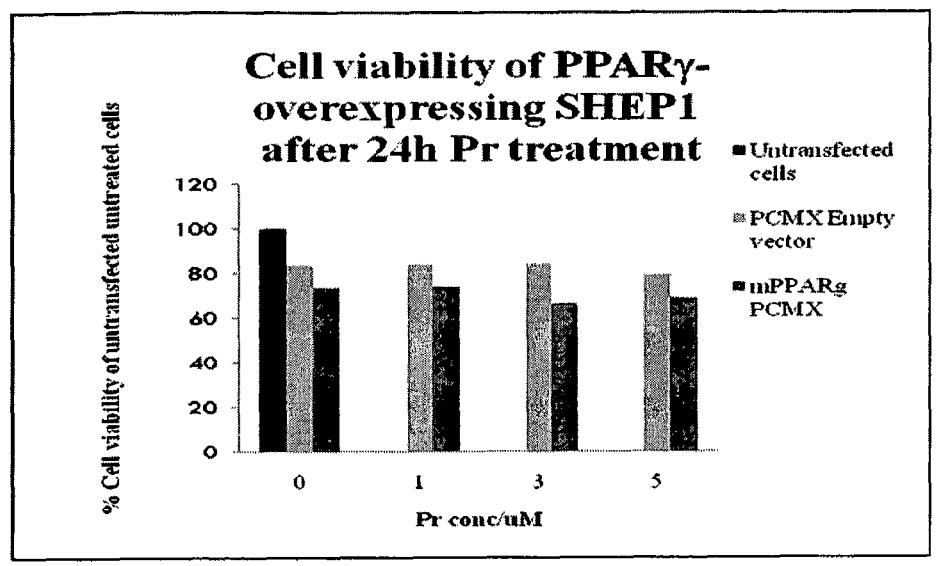
FIG. 10 depicts the cell viability of SHEP1 neuroblastoma cells overexpressing PPARγ that were activated by $C_{19}H_{24}N_3O_5S_5Pr$ (Pr) as described in Example 8. SHEP1 cells were transiently transfected with either an empty vector (indicated as "PCMX empty vector") or a vector encoding wild type PPARγ (indicted as "mPPARg PCMX"). Untransfected cells work as a control. Forty eight hours following transfection, the cells were exposed to increased concentrations (0 to 5 uM) of $C_{19}H_{24}N_3O_5S_5Pr$ (Pr). Cell viability was assessed by MTT assay as described in Example 4.
Figure 11:
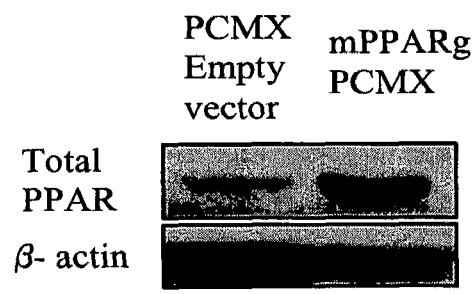
FIG. 11 depicts the results of a Western blot analysis, showing the expression of total PPARγ in "mPPARg PCMX vector" and "PCMX empty vector" (top panel). The expression of β-actin in both "mPPARg PCMX" and "PCMX empty vector" (lower panel) confirmed equivalent total protein blotting.

FIG. 10 shows that overexpression of wild type PPARγ in SHEP1 cells ("mPPARg PCMX") led to a greater decrease in cell viability suggesting that the ability of $C_{19}H_{24}N_3O_5S_5Pr$ to activate PPARγ correlates to cell death. The expression of PPARγ SHEP1 cells transfected with wild type PPARγ is illustrated in FIG. 11.

Example 9

PPARγ Activation by $C_{19}H_{24}N_3O_5S_5Pr$ Abrogated by Overexpressing a DNA Binding-Mutant PPARγ

To determine if $C_{19}H_{24}N_3O_5S_5Pr$ binds to PPARγ, neuroblastoma SHEP1 cells were transiently co-transfected with either empty vector or a DNA-binding mutant of PPARγ, 3×PPPRE luciferase plasmid and renilla plasmid for transfection efficiency. Forty eight hours following transfection, the cells were exposed to increased concentration (0 to 5 uM) of $C_{19}H_{24}N_3O_5S_5Pr$ for 18 hours. PPARγ activity was calculated as luciferase RLU/renilla/µg total protein.

Figure 12:
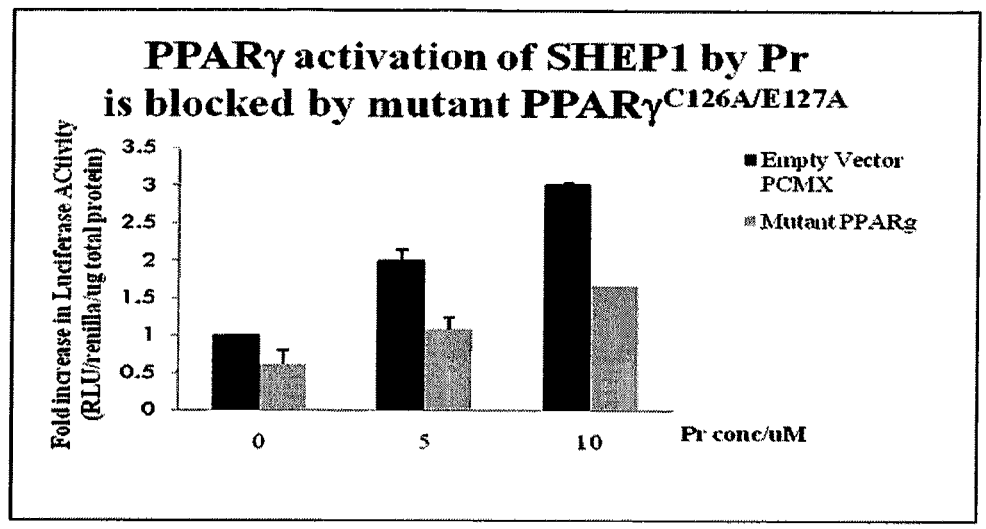
FIG. 12 illustrates the PPARγ activation of SHEP1 neuroblastoma cells that were transiently co-transfected with either empty vector ("Empty Vector PCMX") or a DNA-binding mutant of PPAR gamma ("Mutant PPARg"), together with 3×PPPRE luciferase plasmid and renilla plasmid as described in Example 9. Forty eight hours following transfection, the cells were exposed to increased concentrations (0 to 10 uM) of $C_{19}H_{24}N_3O_5S_5Pr$ (Pr) for 18 hours. PPARγ activity was calculated as luciferase RLU/renilla/μg total protein.
Figure 13:
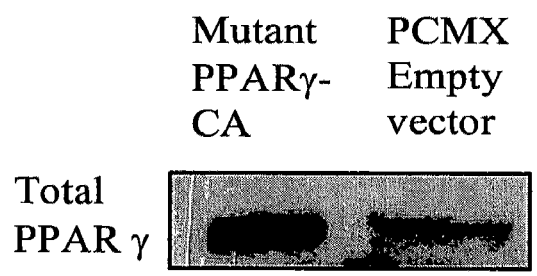
FIG. 13 depicts the results of a Western blot analysis, showing the expression of the DNA-binding mutant of PPARγ (indicated as "Mutant PPARγ-CA") and the expression of PPARγ in "PCMX Empty Vector".

It can be seen from FIG. 12 that overexpression of a DNA-binding mutant PPARγ significantly reduced the ability of $C_{19}H_{24}N_3O_5S_5Pr$ to activate PPARγ. Importantly, the decrease in PPARγ activity is even lower than that observed in cells transfected with empty vector, strongly suggesting that $C_{19}H_{24}N_3O_5S_5Pr$ indeed binds to PPARγ. The expression of PPARγ in "Mutant PPARγ-CA" and in "PCMX Empty Vector" is illustrated in FIG. 13.

Example 10

PPAR-γ Dependence of $C_{19}H_{24}N_3O_5S_5Pr$ is Demonstrated by its Regulation of Bona Fide PPAR-γ Transcriptional Targets in Cancer Cells This example illustrates the effect of $C_{19}H_{24}N_3O_5S_5Pr$ on the expression of PPAR-γ transcriptional targets in cancer cells.

Figure 14A:
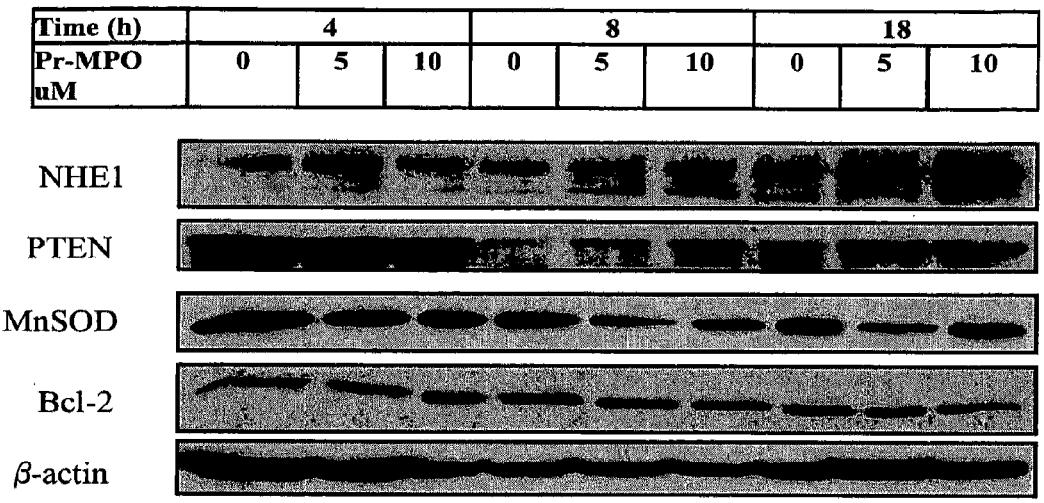
FIGS. 14A & B depict the effect of $C_{19}H_{24}N_3O_5S_5Pr$ (indicated as "Pr-MPO") on the expression of PPAR-γ target proteins (indicated as "NHE1", "PTEN", "MnSOD", "RhoB" and "Bcl-2") in SHEP-1 neuroblastoma cells. The cells were treated with different doses of $C_{19}H_{24}N_3O_5S_5Pr$ (0, 5 and 10 μM of Pr-MPO as indicated) for 4, 8, 18 hr (see FIG. 14A) and 24, 48 and 72 hr (See FIG. 14B). Whole cell extracts were prepared and protein expression was determined by Western Blot analysis. 70 ug of total protein was loaded per lane for each experiment. The levels of the respective protein were determined by using specific primary antibody followed by peroxidise-conjugated secondary antibody and visualization with enhanced chemiluminescence. β-actin was used as a control to confirm equivalent total protein blotting.
Figure 14B:
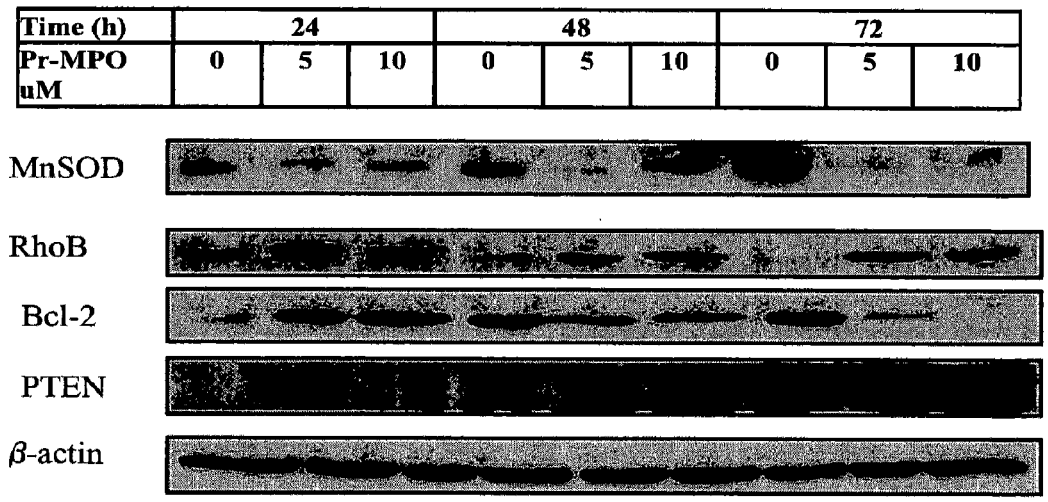
Figure 15:
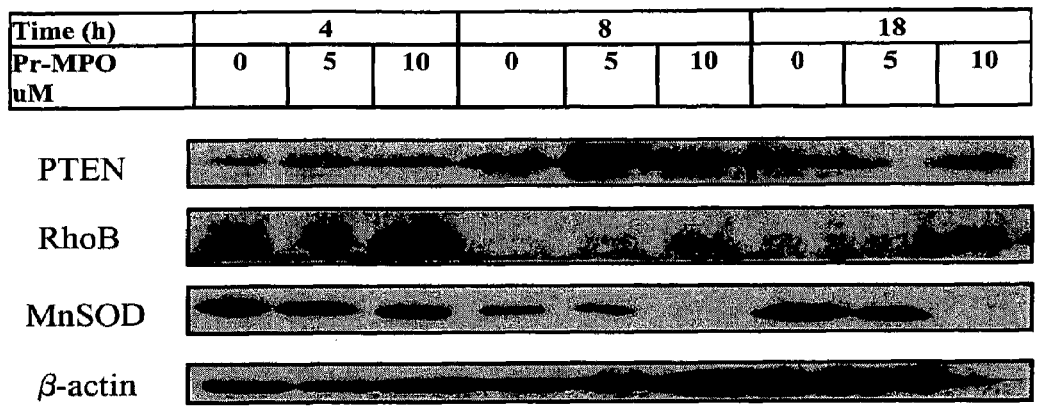
FIG. 15 depicts the effect of $C_{19}H_{24}N_3O_5S_5Pr$ (indicated as "Pr-MPO") on the expression of PPAR-γ target proteins (indicated as "PTEN", "RhoB", "MnSOD") in MDA-MB-231 breast cancer cells. The cells were treated with different doses of $C_{19}H_{24}N_3O_5S_5Pr$ (0, 5 and 10 μM of Pr-MPO as indicated) for 4, 8 and 18 hr.

Referring to FIGS. 14 and 15, SHEP-1 neuroblastoma cells and MDA-MB-231 breast cancer cells were treated with different concentrations of $C_{19}H_{24}N_3O_5S_5Pr$ at 5 µM and 10 µM for 4 hr, 8 hr, 18 hr, 24 lr, 48 hr and 72 hr. Whole cell extracts were prepared and protein expression was examined by Western Blot analysis. 70 µg of total protein was loaded per lane for each experiment. The levels of protein were determined by using specific primary antibody followed by peroxidise-conjugated secondary antibody and visualization by enhanced chemiluminescence.

As depicted in both FIGS. 14 and 15, $C_{19}H_{24}N_3O_5S_5Pr$ regulates the expression of PPAR-γ transcriptional targets, namely PTEN (phosphotase and tensin homologue), RhoB (Ras homolog gene family, member B) and MnSOD (manganese superoxide dismutase) in both SHEP-1 and MDA-MB-231 cancer cell lines in a dose-dependent manner. In particular, PTEN and RhoB were upregulated, and MnSOD was downregulated by $C_{19}H_{24}N_3O_5S_5Pr$.

Figure 16:
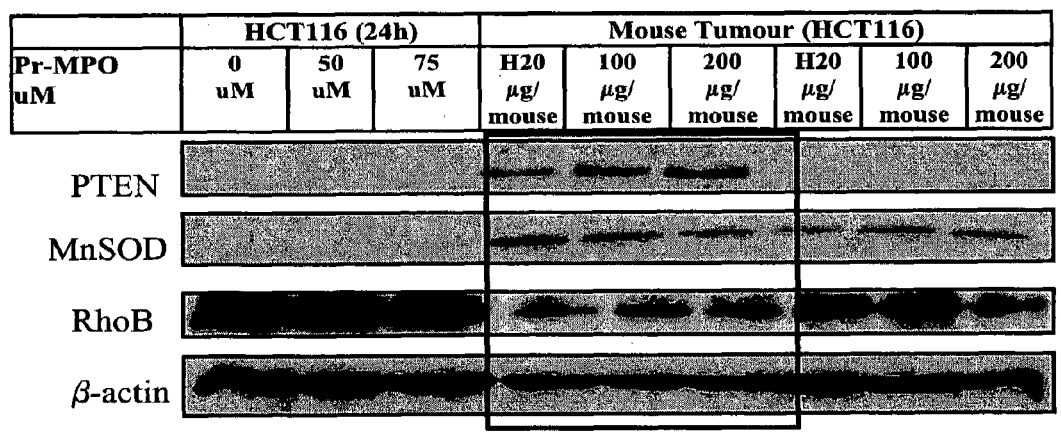
FIG. 16 depicts the effects of PPAR-γ target proteins, PTEN, MnSOD and RhoB in HCT-116 mouse tumors. HCT-116 colorectal tumor cells were grafted onto nude mice. The tumor-bearing mice were then treated with solvent control ("indicated as $H_2O$") or the different concentrations of $C_{19}H_{24}N_3O_5S_5Pr$ (indicated as "Pr-MPO") as indicated as 100 μg/mouse or 200 μg/mouse. After 21 days of treatment, the mice were sacrificed, after which tumors were harvested and proteins extracted for Western Blot analysis. Similar to results demonstrated in SHEP-1 and MDA-MB-231 cancer cell lines, PPAR-γ target proteins PTEN, RhoB and MnSOD are regulated by Pr-MPO in mouse tumor (as indicated by the rectangle).
Figure 17:
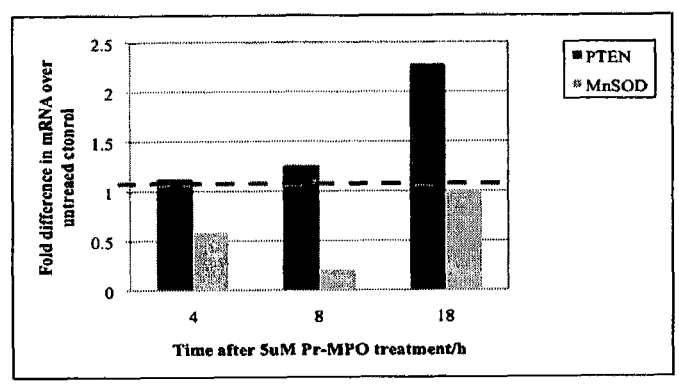
FIG. 17 depicts a graph demonstrating the effect of $C_{19}H_{24}N_3O_5S_5Pr$ (indicated as "Pr-MPO treatment") on mRNA levels of PTEN (shaded box) and MnSOD (unshaded box) in SHEP-1 cells after 4 hr, 8 hr and 18 hr. To demonstrate that PTEN and MnSOD are modulated by Pr-MPO at the transcriptional level, mRNA levels of PTEN and MnSOD were assayed by real time PCR after treatment with 10 uM Pr-MPO for 4 hr, 8 hr and 18 hr.

Referring to FIG. 16, $C_{19}H_{24}N_3O_5S_5Pr$ also regulates the expression of PPAR-γ transcriptional targets in HCT-116 mouse tumors. HCT-116 colorectal tumor cells were grafted onto nude mice. Tumor-bearing mice were then treated with solvent control or different concentrations of (100 µg, 200 µg) $C_{19}H_{24}N_3O_5S_5Pr$. After 21 days of treatment, the mice were sacrificed, after which tumors were harvested and proteins extracted for Western Blot analysis. Similar to results demonstrated in SHEP-1 and MDA-MB-231 cancer cell lines, PPAR-γ target proteins PTEN, RhoB and MnSOD were regulated by $C_{19}H_{24}N_3O_5S_5Pr$ in mouse tumors.

Therefore, this example provides strong evidence that $C_{19}H_{24}N_3O_5S_5Pr$ induces PPAR-γ dependent effects, as shown by the transcriptional modulation of bona fide PPAR-γ target genes.

Example 11 mRNA Levels of PTEN and MnSOD after Pr-MPO Treatment

This example illustrates the effect of $C_{19}H_{24}N_3O_5S_5Pr$ on the mRNA levels of PTEN and MnSOD in SHEP-1 cancer cells. mRNA levels of PTEN and MnSOD were assayed by real time PCR after treatment with 10 uM Pr-MPO for 4 hr, 8 hr and 18 h.

As shown in FIG. 17, real-time PCR results demonstrates that the modulation of PPAR-γ transcriptional targets observed at the protein level were also found at the mRNA level.

Example 12

Induction of RhoB by $C_{19}H_{24}N_3O_5S_3Pr$

This example shows that effect of $C_{19}H_{24}N_3O_5S_5Pr$ on the induction of RhoB protein in SHEP-1 cancer cells, when preincubated with a specific PPAR-γ antagonist.

Figure 18:
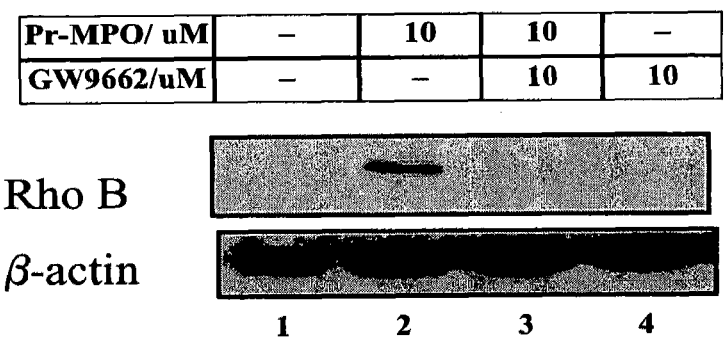
FIG. 18 depicts the abrogation of the expression of RhoB in SHEP-1 cancer cells, after the cells were preincubated with 10 uM of GW9662, a specific PPAR-γ antagonist or a vehicle control for 2 hrs, before the cells were being exposed to 10 uM $C_{19}H_{24}N_3O_5S_5Pr$ ("Pr-MPO") for 4 hours. Lanes 1 and 4 act as controls. Lane 2 shows the expression of Rho B after SHEP-1 cells were exposed to $C_{19}H_{24}N_3O_5S_5Pr$. Lane 3 shows the abrogation of Rho B in SHEP-1 cells due to the preincubation of GW9662, prior to being exposed to $C_{19}H_{24}N_3O_5S_5Pr$.

SHEP-1 cancer cells were preincubated with 10 uM GW9662, a pharmacological PPAR-γ antagonist that was able to abrogate the induction of RhoB protein by $C_{19}H_{24}N_3O_5S_5Pr$, or vehicle control for 2 hours before being exposed to 10 uM of $C_{19}H_{24}N_3O_5S_5Pr$ for 4 hours. As shown in FIG. 18 (see lane 3), RhoB was not expressed, indicating the abrogation of RhoB in SHEP-1 cancer cells, thereby providing evidence that transcriptional upregulation of this target protein is dependent upon PPAR-γ activation.

Example 13

Activation of PPAR-γ by $C_{19}H_{24}N_3O_5S_5Pr$ Using Luciferase Reporter Assay This example shows that $C_{19}H_{24}N_3O_5S_5Pr$ activates PPARγ receptor by ligand binding. Two different methods were employed as shown in the following.

Figure 19A:
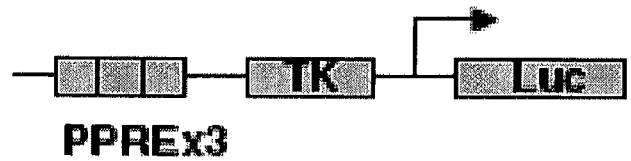
FIG. 19A shows a schematic representation of a reporter plasmid containing three copies of the PPAR response element ("pPPREx3-TKLuc") that was used for transfection into SHEP-1 cancer cells in Method 1 as described in Example 13.
Figure 19B:
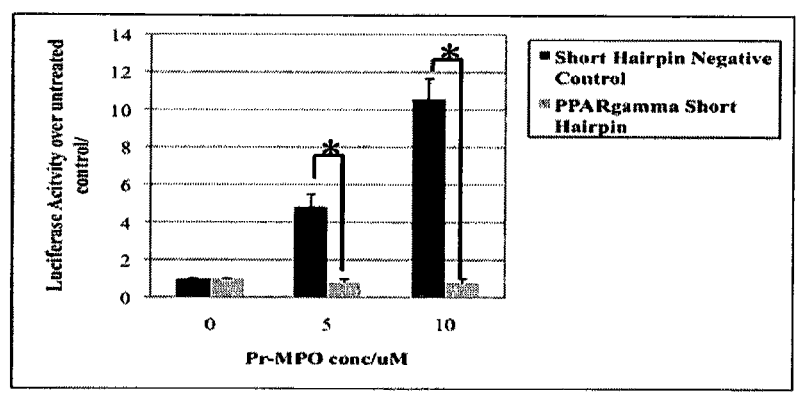
FIG. 19B measures the luciferase activity in SHEP-1 cells in which PPAR-γ activation by $C_{19}H_{24}N_3O_5S_5Pr$ ("Pr-MPO") was abrogated by PPAR-γ-silencing using short-hairpin RNA plasmid transfection. SHEP-1 cells were transiently transfected with either short-hairpin RNA plasmid targeting PPAR-γ protein or short hairpin RNA negative control, 3×PPRE luciferase reporter and renilla plasmids (as transfection control). Cells were exposed to varying doses (5 uM, 10 uM) of Pr-MPO for 18 h.
Figure 19C:
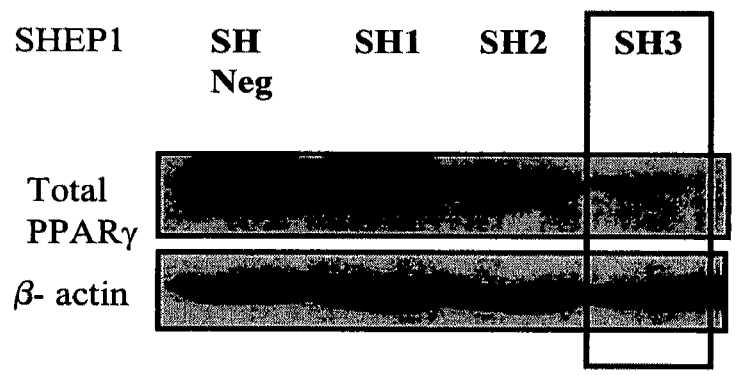
FIG. 19C depicts a Western Blot showing the silencing of PPAR-γ after 48 h transfection of short-hairpin RNA plasmids with varying sequences targeting PPAR-γ. SH3 was used for subsequent silencing experiments as it is the most effective plasmid for PPAR-γ knock-down, as shown in the Western Blot.

In Method 1, a reporter plasmid containing three copies of the PPAR response element (pPPREx3-TKLuc) as illustrated in FIG. 19A and as previously described in Kim et al, Toxicological Sciences, 85, (2005), pp. 585-593, was transfected into SHEP-1 cancer cells. This system directly measures activation of endogenous PPAR via transcriptional activation of the luciferase reporter gene as a result of PPARγ binding to the PPAR response element (PPRE). To determine whether PPARγ receptor is activated by $C_{19}H_{24}N_3O_5S_5Pr$, the SHEP-1 cancer cells was transiently transfected with either short-hairpin RNA plasmid targeting PPAR-γ protein or short hairpin RNA negative control. The cells were exposed to varying doses (5 uM, 10 uM) of $C_{19}H_{24}N_3O_5S_5Pr$ for 18 hr. As shown in FIG. 19A, upon silencing of PPARγ protein by short-hairpin RNA plasmid transfection, $C_{19}H_{24}N_3O_5S_5Pr$-induced luciferase activity was abrogated.

Figure 20A:
FIG. 20A shows a schematic representation of chimeric receptors (pCMX-Gal-mPPARα-LBD for PPARα and pCMX-GalmPPARδ-LBD for PPARδ and a reporter plasmid containing four copies of a Gal4 binding site ("pMH100X4-TK-Luc") used in Method 2 as described in Example 13.
Figure 20A:
Figure 20B:
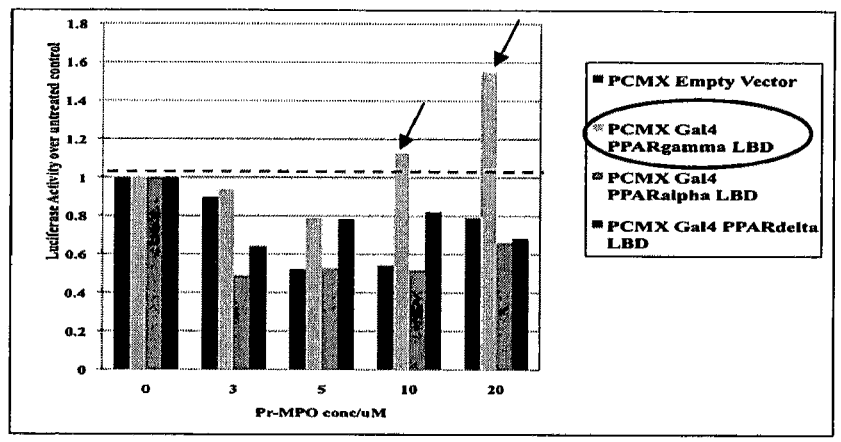
FIG. 20B measures the luciferase activity in SHEP-1 cells in which the cells were transfected with a) a chimeric receptor of a single PPAR isoform "pCMX-Gal-mPPARα-LBD", b) pCMX-Gal-mPPARδ-LBD, or c) pCMX-Gal-mPPARγ-LBD, followed by exposure to $C_{19}H_{24}N_3O_5S_5Pr$ ("Pr-MPO") at different concentrations of 3 μM, 5 μM, 10 μM and 20 μM. In this system, once Pr-MPO binds to the ligand binding domain (LBD) of either PPARα, PPARδ or PPAR-γ of the chimeric receptor, the DNA binding domain of the yeast Gal4 (denoted as "Gal") would bind to co-transfected Gal4 binding site, initiating transcription of the firefly luciferase. Renilla plasmid was also transfected as an internal control.

In Method 2, SHEP-1 cancer cells were transfected with a reporter gene containing four copies of a Gal4 binding site (pMH100x4-TK-Luc) and chimeric receptors of a single PPAR isoform (pCMX-Gal-mPPARα-LBD, pCMX-Gal-mPPARδ-LBD, or pCMX-Gal-mPPARγ-LBD, respectively) as previously described in Kim et al, *Toxicological Sciences*, 85, (2005), pp. 585-593. When $C_{19}H_{24}N_3O_5S_5Pr$ binds to the ligand binding domain (LBD) of the chimeric receptor, the DNA binding domain of Gal4 binds to co-transfected Gal4 binding site and initiates transcription of the firefly luciferase. As shown in FIG. 20B, induction of luciferase activity by $C_{19}H_{24}N_3O_5S_5Pr$ ("Pr-MPO") was observed in cells transfected with pCMX-Gal-mPPARγ-LBD (indicated by the arrows), suggesting strongly that $C_{19}H_{24}N_3O_5S_5Pr$ is a PPARγ ligand.

Example 14

Figure 21A:
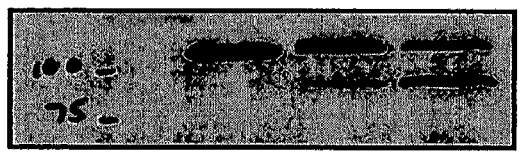
FIG. 21A shows the PARP cleavage in SHEP-1 cells after 24 hr treatment with $C_{19}H_{24}N_3O_5S_5Pr$ (indicated as "Pr-MPO") as evidenced by the formation of the 80 kDa fragment shown in the Western Blot, when the cells were treated with 5 μM and 10 μM of Pr-MPO respectively.

Induction of PARP Cleavage, Bax Translocation, Cytochrome C Release, and Translocation of Apoptosis Inducing Factor by $C_{19}H_{24}N_2O_5S_5Pr$ To demonstrate the induction of PARP cleavage by $C_{19}H_{24}N_3O_5S_5Pr$ in SHEP-1 cancer cells, the cells were treated with to 5 μM and 10 μM $C_{19}H_{24}N_3O_5S_5Pr$. After 24 hrs, the treated cells were analysed by Western Blot analysis to detect the formation of the 80 kDa fragment as shown in FIG. 21A, thereby indicating PARP cleavage.

Figure 21B:
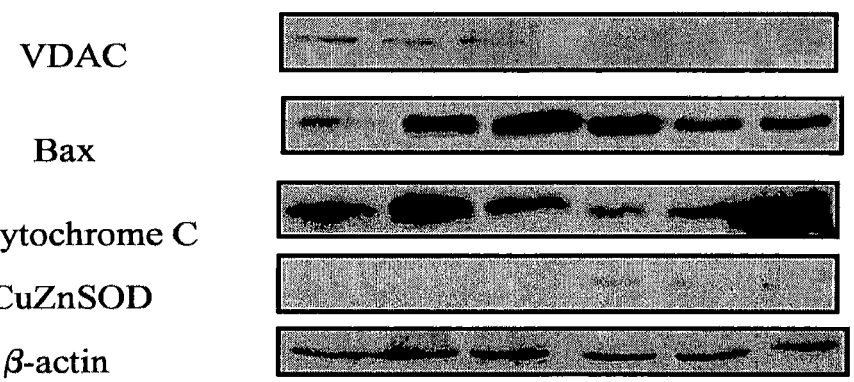
FIGS. 21B and C show the effect of different concentrations (5 μM and 10 μM) of $C_{19}H_{24}N_3O_5S_5Pr$ (indicated as "Pr-MPO") on SHEP-1 cells in which Pr-MPO causes Bax translocation to the mitochondrial fraction as well as cytochrome C release into the cytosol after 18 hr and 24 hr treatment respectively. The expression of voltage-dependent anion channel (VDAC) and Cu/Zn superoxide dismutase (CuZnSOD) were used as controls. β-actin was used as a control to confirm equivalent total protein blotting.
Figure 21C:
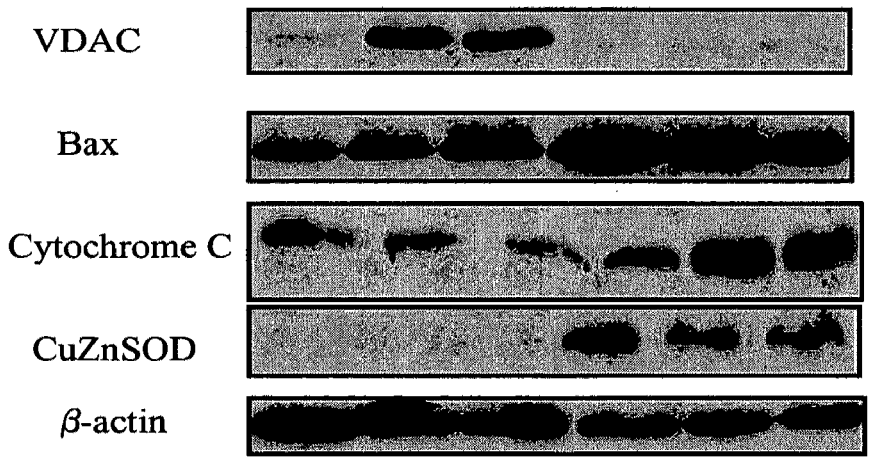

To demonstrate the induction of Bax translocation into the mitochondrial fraction and cytochrome C release into the cytosol of SHEP-1 and SHSY5Y cancer cells, different concentrations (5 μM and 10 μM) of $C_{19}H_{24}N_3O_5S_5Pr$ (indicated as "Pr-MPO) were administered into the respective cancer cells. As shown in FIGS. 21B and C, $C_{19}H_{24}N_3O_5S_5Pr$ causes Bax translocation to the mitochondrial fraction and cytochrome C release into the cytosol in SHEP-1 cancer cells, after 18 hr and 24 hr treatment respectively. As shown in FIG. 22, $C_{19}H_{24}N_3O_5S_5Pr$ causes Bax translocation to the mitochondrial fraction and cytochrome C release into the cytosol in SHSY5Y neuroblastoma cells.

Although the inventors have found that $C_{19}H_{24}N_3O_5S_5Pr$ causes MOMP (mitochondrial outer membrane permeabilization) as evidenced by Bax translocation and cytochrome C release into cytosol, the inventors found that $C_{19}H_{24}N_3O_5S_5Pr$ does not activate caspases in cancer cells.

To characterize the mode of caspase-independent cell death induced by $C_{19}H_{24}N_3O_5S_5Pr$, the possibility of autophagic cell death as well as the possible involvement of AIF (apoptosis inducing factor) was investigated, in view of previous findings that AIF trigger caspase-independent cell death (see for example, Candé et al, *Journal of Cell Science*, 115, 4727-4734 (2002); and Lorenzo H K et al, Cell Death and Differentiation, 6, 516-524 (1999).

Different concentrations (5 μM and 10 μM) of $C_{19}H_{24}N_3O_5S_5Pr$ (indicated as "Pr-MPO") were administered into SHEP-1 cancer cells. The detection of AIF in the cytosol and nucleus fractions was determined by Western Blot analysis at 18 hr and 24 hr of treatment with $C_{19}H_{24}N_3O_5S_5Pr$. As shown in FIG. 23, AIF was translocated into the nucleus 24 hr after treatment with Pr-MPO.

Example 15

Caspase-Independent Cell Death as Evidenced by LC3-II Formation after $C_{19}H_{24}N_3O_5S_5Pr$ Treatment The appearance of the phosphtidylethaonolamine (PE)-conjugated form of microtubule-associated protein 1 light chain 3 (LC3-II) is a marker of autophagy as described in for example Kabeya Y, *European Molecular Biology Organization*, 19(21), 5720-5728, 2000, as it has been shown to play an early and critical role in autophagosomes formation.

Figure 24A:
FIGS. 24A and B show the induction of phosphtidylethanonolamine (PE)-conjugated form of microtubule-associated protein 1 light chain 3 (LC3 II) by administering different concentrations (5 μM, 10 μM) of $C_{19}H_{24}N_3O_5S_5Pr$ (indicated as "Pr-MPO") into SHEP-1 cells (A) and in SHSY5Y cells (B), and detecting the expression of LC3II by Western Blot at 4 hr, 8 hr and 18 hr of $C_{19}H_{24}N_3O_5S_5Pr$ treatment. (LC3 I) is a cytosolic form of microtubule-associated protein 1 light chain 3. β-actin was used as a control to confirm equivalent total protein blotting.
Figure 24B:
FIG. 24C shows the effect of reversing the induction of LC3II by 3-methyl adenine (3MA), an inhibitor of autophagy. SHSY5Y cells were preincubated with vehicle control or 5 or 10 mM of 3MA for 2 hours, followed by treatment with 10 uM $C_{19}H_{24}N_3O_5S_5Pr$ (indicated as "Pr-MPO") for 7 hours. LC3 II levels were reduced by preincubation with 3MA, as shown by the last two lanes of the Western Blot.

To demonstrate that $C_{19}H_{24}N_3O_5S_5Pr$ induces LC3 II (microtubule-associated protein 1 light chain 3) formation, which is a classical marker of autophagy as described above, SHEP-1 and SHSY5Y cancer cells were exposed to (5 μM and 10 μM) of $C_{19}H_{24}N_3O_5S_5Pr$. The expression of LC3 I and LC3 II in SHEP-1 and SHSY5Y cancer cells were detected by Western Blotting at 4 hr, 8 hr and 18 hr after $C_{19}H_{24}N_3O_5S_5Pr$ treatment as shown in FIGS. 24A and B respectively.

Figure 24C:
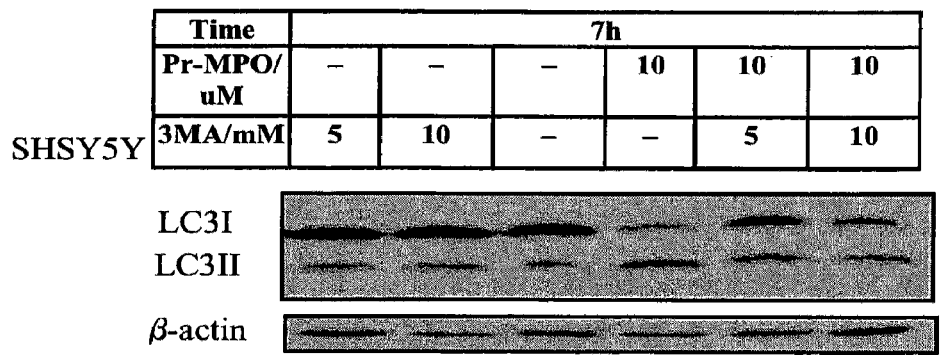

To demonstrate that $C_{19}H_{24}N_3O_5S_5Pr$ might induce canonical autophagy involving PI3K pathway, SHSY5Y cancer cells were preincubated with vehicle control or 5 or 10 mM of 3-methyladenine (3MA) to reverse the formation of LC3 II for 2 hours, followed by treatment with 10 uM $C_{19}H_{24}N_3O_5S_5Pr$ for 7 hours. As shown in FIG. 24C, LC3 II levels were reduced by preincubation with 3MA (see last two lanes in Western Blot of FIG. 24C).

Example 16

Morphological Changes Induced by $C_{19}H_4N_3O_5S_5Pr$ are Reversed by 3MA

Figure 25A:
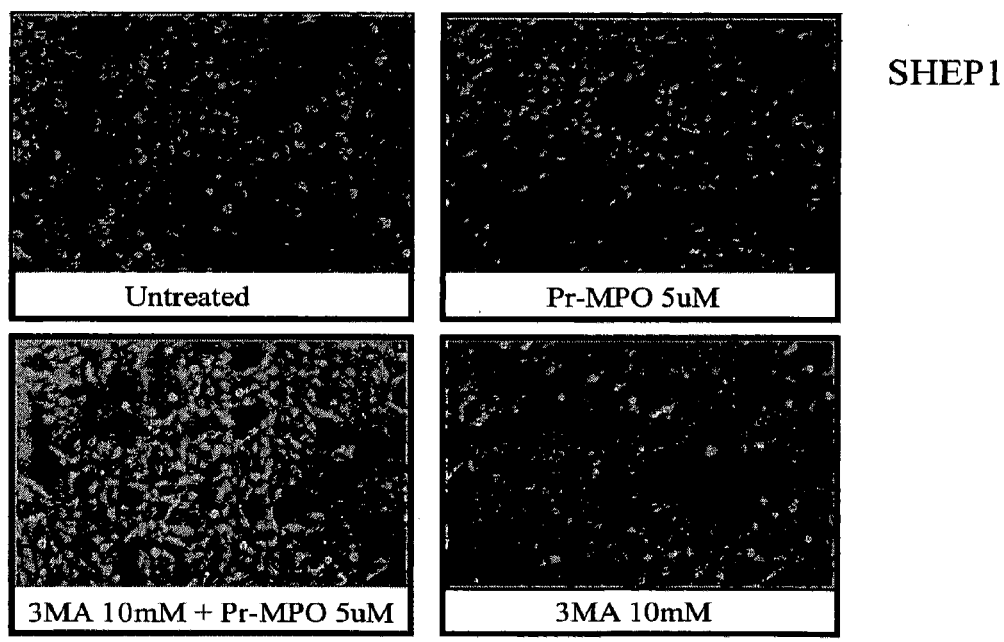
FIG. 25A shows the microscopic images of SHEP-1 cells preincubated with 10 mM of 3MA followed by 5 μM of $C_{19}H_{24}N_3O_5S_5Pr$ (indicated as "3MA 10 mM+Pr-MPO 5 uM"); as compared to untreated cells (indicated as "untreated"); cells treated with $C_{19}H_{24}N_3O_5S_5Pr$ only (indicated as "Pr-MPO 5 uM"); and cells preincubated with 10 mM of 3MA only (indicated as "3MA 10 mM").
Figure 25B:
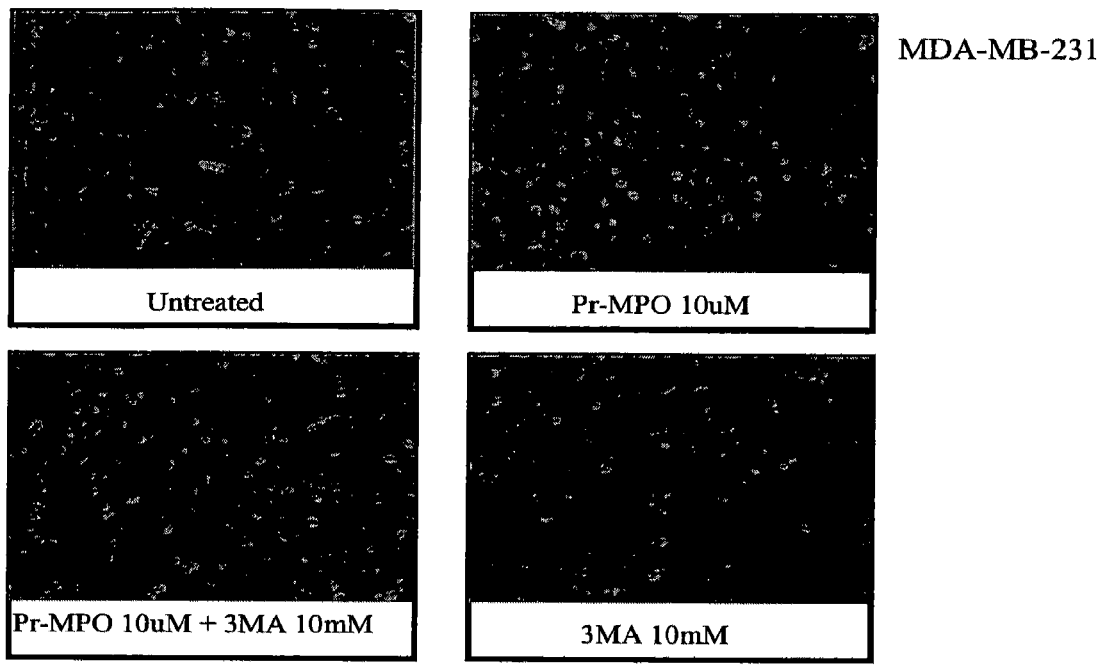
FIG. 25B shows the microscopic images of MDA-MB-231 cells preincubated with 10 mM of 3MA followed by 10 uM of $C_{19}H_{24}N_3O_5S_5Pr$ (indicated as "Pr-MPO 10 uM+3MA 10 mM"); as compared to untreated cells (indicated as "untreated"); cells treated with $C_{19}H_{24}N_3O_5S_5Pr$ only (indicated as "Pr-MPO 10 uM"); and cells preincubated with 10 mM of 3MA only (indicated as "3MA 10 mM").

To demonstrate the morphological changes in cancer cells induced by $C_{19}H_{24}N_3O_5S_5Pr$ in the presence of 3MA, SHEP-1 cancer cells were preincubated with 10 mM of 3MA followed by 5 μM of $C_{19}H_{24}N_3O_5S_5Pr$ (indicated as "3MA 10 mM+Pr-MPO 5 uM" in FIG. 25A). MDA-MB-231 cancer cells were preincubated with 10 mM of 3MA followed by 10 μM of $C_{19}H_{24}N_3O_5S_5Pr$ (indicated as "Pr-MPO 10 μM+3MA 10 mM").

As shown in FIGS. 25A and B, SHEP-1 and MDA-MB-231 cancer cells treated with $C_{19}H_{24}N_3O_5S_5Pr$ alone were rounded up and also lower in cell density (indicated as "Pr-MPO 5 μM" and "Pr-MPO 10 μM"). Cells preincubated with 3MA (indicated as "3MA 10 mM+Pr-MPO 5 uM" and "Pr-MPO 10 μM+3MA 10 mM") however, did not demonstrate this death-like morphology, suggesting that $C_{19}H_{24}N_3O_5S_5Pr$ might be inducing autophagic cell death.

Example 17

Effect of $C_{19}H_{24}N_3O_5S_5Pr$ on HCT-116 Colorectal Tumor Cells in Mice

This example illustrates the tumor activity of HCT-116 colorectal cancer cells in mice when treated with $C_{19}H_{24}N_3O_5S_5Pr$.

Figure 26A:
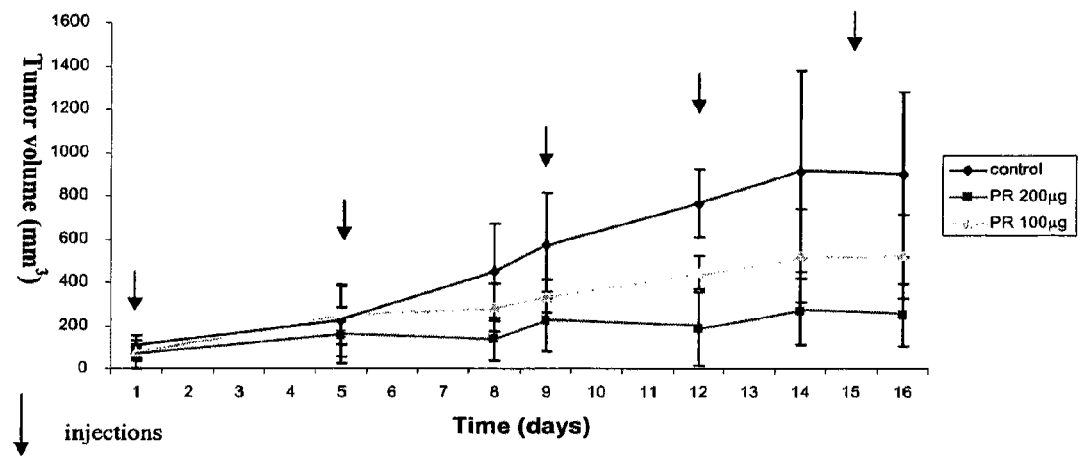
FIGS. 26A and B show the effect of $C_{19}H_{24}N_3O_5S_5Pr$ on HCT-116 colorectal cancer cells in mice. "Control" refers to mice treated with water. "PR 200 ug" refers to mice treated with 200 ug of $C_{19}H_{24}N_3O_5S_5Pr$. "PR 100 ug" refers to mice treated with 100 ug of $C_{19}H_{24}N_3O_5S_5Pr$. The arrows indicated on the graph refer to the day on which the mice were injected with the respective concentration (100 ug or 200 ug) of $C_{19}H_{24}N_3O_5S_5Pr$ or with water. Tumor volume was measured in $mm^3$.
Figure 26B:
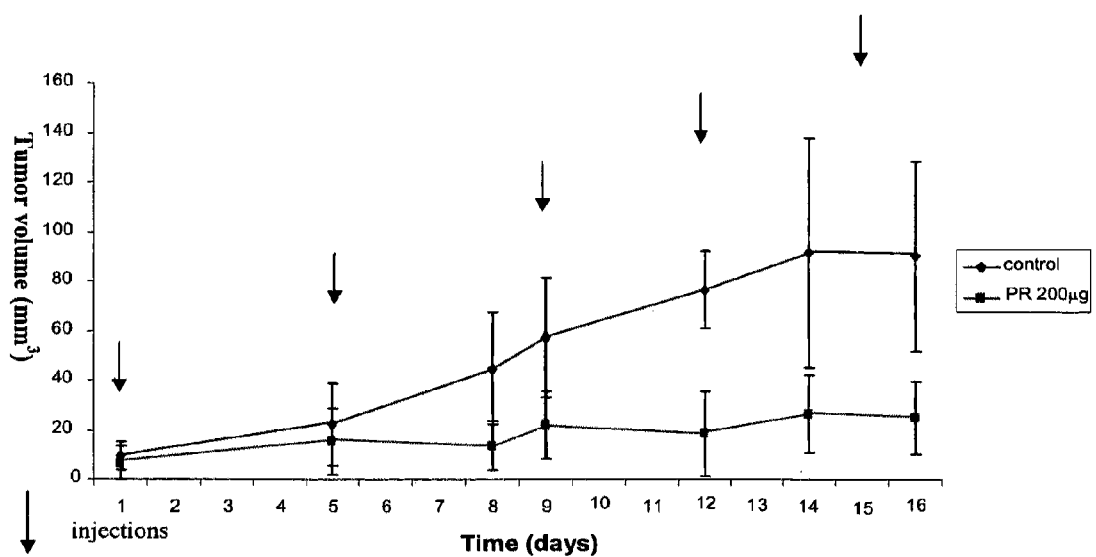

HCT-116 colorectal tumor cells were grafted subcutaneously onto nude mice. Tumor-bearing mice were then treated with solvent control (water) or different concentrations of (100 μg, 200 μg) $C_{19}H_{24}N_3O_5S_5Pr$ on day 1, day 5, day 9, day 12, and day 15. Tumor volumes ($mm^3$) were measured on day 1, day 5, day 8, day 9, day 12, day 14 and day 16. Tumor volumes in treated mice were compared with those of control mice. As shown in FIGS. 26A and B, mice treated with $C_{19}H_{24}N_3O_5S_5Pr$ did not show a substantial increase in tumor size when compared to control mice. In particular, the tumor growth suppression/inhibition induced by 200 μg of $C_{19}H_{24}N_3O_5S_5Pr$ was at least 3 fold more than that of control mice. In addition, it can be seen that the tumor activity was suppressed/inhibited by at least 2 fold when the dosage of $C_{19}H_{24}N_3O_5S_5Pr$ was increased from 100 μg to 200 μg.

The listing or discussion of a previously published document in this specification should not necessarily be taken as an acknowledgement that the document is part of the state of the art or is common general knowledge. All documents listed are hereby incorporated herein by reference in their entirety.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognise that the invention is also thereby described in terms of any individual member or subgroup of members of the Markush group.

What is claimed is:

1. A pharmaceutical composition comprising
   (a) praseodymium(2-mercaptopyridine N-oxide)(dimethyl sulfoxide);
   (b) a carrier or diluent; and
   (c) an estrogen receptor modulator.

* * * * *

UNITED STATES PATENT AND TRADEMARK OFFICE
CERTIFICATE OF CORRECTION

PATENT NO.       : 8,691,851 B2  
APPLICATION NO.  : 13/262561  
DATED            : April 8, 2014  
INVENTOR(S)      : Shazib Pervaiz Page 1 of 1

It is certified that error appears in the above-identified patent and that said Letters Patent is hereby corrected as shown below:

In the Specification

In column 21, line 27:
  "5-cytarabine (Cytosar-U®, Depo-Cyt®)" should be
  --5-fluorouracil (Adrucil®), 6-thioguanine (Thioguanine®), hydroxyurea (Hydrea®), cytarabine (Cytosar-U®, Depo-Cyt®)--.

In column 27, line 45: "24 1r" should be --24 hr--.

Signed and Sealed this
Twelfth Day of August, 2014

Michelle K. Lee
*Deputy Director of the United States Patent and Trademark Office*